United States Patent [19]
Barbosa et al.

[11] Patent Number: 5,981,188
[45] Date of Patent: Nov. 9, 1999

[54] METHOD FOR IDENTIFYING AGENTS THAT MODULATE TRANSCRIPTION OF HUMAN CYTOMEGALOVIRUS POLYMERASE

[75] Inventors: Miguel S. Barbosa; Jun Wu, both of San Diego, Calif.

[73] Assignee: Signal Pharmaceuticals, Inc., San Diego, Calif.

[21] Appl. No.: 08/939,028

[22] Filed: Sep. 26, 1997

Related U.S. Application Data

[63] Continuation-in-part of application No. 08/720,543, Sep. 30, 1996.

[51] Int. Cl.$^6$ .................................................... C12Q 1/68
[52] U.S. Cl. ................................................................ 435/6
[58] Field of Search .................................. 435/6; 536/24.1

[56] References Cited

U.S. PATENT DOCUMENTS 4,743,562  5/1988  Rasmussen et al. ..................... 436/518
5,418,132  5/1995  Olivo ......................................... 435/5

FOREIGN PATENT DOCUMENTS 521 427 A1  1/1993  European Pat. Off. .

OTHER PUBLICATIONS

Kerry et al., "Identification of Sequence Elements in the Human Cytomegalovirus DNA Polymerase Gene Promotor Required for Activation by Viral Gene Products," *Journal of Virology* 68(7):4167–4176, 1994.
Kerry et al., "Multiple Regulatory Events Influence Human Cytomegalovirus DNA Polymerase (UL54) Expression during Viral Infection," *Journal of Virology* 70(1):373–382, 1996.
Arlt et al., "Identification of Binding Sites for the 86–Kilodalton IE2 Protein of Human Cytomegalovirus within an IE2–Responsive Viral Early Promoter," *Journal of Virology* 68(7):4117–4125, 1994.
Klucher et al., "In Vivo and In Vitro Analysis of Transcriptional Activation Mediated by the Human Cytomegalovirus Major Immediate–Early Proteins," *Molecular and Cellular Biology* 13(2):1238–1250, 1993.
Lang et al., "Functional Interaction between the Human Cytomegalovirus 86–Kilodalton IE2 Protein and the Cellular Transcription Factor CREB," *Journal of Virology* 69(10):6030–6037, 1995.
Plachter et al., "Cell Types Involved in Replication and Distribution of Human Cytomegalovirus," *Advances in Virus Research* 46:195–261, 1996.
Baracchini et al., "An Isoform Variant of the Cytomegalovirus Immediate–Early Auto Repressor Functions as a Transcriptional Activator," *Virology* 188:518–529, 1992.

Depto and Stenberg, "Functional Analysis of the True Late Human Cytomegalovirus pp28 Upstream Promotor: cis–Acting Elements and Viral trans–Acting Proteins Necessary for Promoter Activation," *Journal of Virology* 66(5):3241–3246, 1992.
Depto and Stenberg, "Regulated Expression of the Human Cytomegalovirus pp65 Gene: Octamer Sequence in the Promoter Is Required for Activation by Viral Gene Products," *Journal of Virology* 63(3):1232–1238, 1989.
Gribaudo et al., "Interferons Inhibit Onset of Murine Cytomegalovirus Immediate–Early Gene Transcription," *Virology* 197:303–311, 1993.
Hagemeier et al., "The 72K IE1 and 80K IE2 proteins of human cytomegalovirus independently trans–activate the c–fos, c–myc and hsp70 promoters via basal promoter elements," *Journal of General Virology* 73:2385–2393, 1992.
Hagemeirer et al., "The Human Cytomegalovirus 80–Kilodalton but Not the 72–Kilodalton Immediate–Early Protein Transactivates Heterologous Promoters in a TATA Box–Dependent Mechanism and Interacts Directly with TFIID," *Journal of Virology* 66(7):4452–4456, 1992.
Hermiston et al., "Identification and Characterization of the Human Cytomegalovirus Immediate–Early Region 2 Gene That Stimulates Gene Expression from an Inducible Promoter," *Journal of Virology* 61(10):3214–3221, 1987.
Iskenderian et al., "Four of Eleven Loci Required for Transient Complementation of Human Cytomegalovirus DNA Replication Cooperate To Activate Expression of Replication Genes," *Journal of Virology* 70(1):383–392, 1996.
Jenkins et al., "Human cytomegalovirus late protein encoded by ie2: a trans–activator as well as a repressor of gene expression," *Journal of General Virology* 75:2337–2348, 1994.
Kohler et al., "Use of Recombinant Virus To Assess Human Cytomegalovirus Early and Late Promoters in the Context of the Viral Genome," *Journal of Virology* 68(10):6589–6597, 1994.
Leach and Mocarski, "Regulation of Cytomegalovirus Late–Gene Expression: Differential Use of Three Start Sites in the Transcriptional Activation of ICP36 Gene Expression," *Journal of Virology* 63(4):1783–1791, 1989.

(List continued on next page.)

*Primary Examiner*—Nancy Degen
*Assistant Examiner*—Thomas G. Larson
*Attorney, Agent, or Firm*—Seed and Berry LLP

[57] ABSTRACT

Compositions and methods are provided for identifying proteins and other agents that modulate transactivation of HCMV early genes. In particular, agents that inhibit the cell-type specific transactivation of HCMV DNA polymerase are provided. Such agents may be used, for example, in the treatment of patients infected with HCMV.

2 Claims, 17 Drawing Sheets

OTHER PUBLICATIONS

Lukac et al., "Transcriptional Activation by the Human Cytomegalovirus Immediate–Early Proteins: Requirements for Simple Promoter Structures and Interactions with Multiple Components of the Transcription Complex," *Journal of Virology* 68(8):5184–5193, 1994.

Platcher et al., "Analysis of Proteins Encoded by IE Regions 1 and 2 of Human Cytomegalovirus Using Monoclonal Antibodies Generated against Recombinant Antigens," *Virology* 193:642–652, 1993.

Rüger et al., "Primary Structure and Transcription of the Genes Coding for the Two Virion Phosphoproteins pp65 and pp71 of Human Cytomegalovirus," *Journal of Virology* 61(2):446–453, 1987.

Scully et al., "The Human Cytomegalovirus IE2 86–Kilodalton Protein Interacts with an Early Gene Promoter via Site–Specific DNA Binding and Protein–Protein Associations," *Journal of Virology* 69(10):6533–6540, 1995.

Stasiak and Mocarski, "Transactivation of the Cytomegalovirus ICP36 Gene Promoter Requires the α Gene Product TRS1 in Addition to IE1 and IE2," *Journal of Virology* 66(2):1050–1058, 1992.

Stenberg et al., "Promoter–Specific trans Activation and Repression by Human Cytomegalovirus Immediate–Early Proteins Involves Common and Unique Protein Domains," *Journal of Virology* 64(4):1556–1565, 1990.

Stenberg et al., "Regulated Expression of Early and Late RNAs and Proteins from the Human Cytomegalovirus Immediate–Early Gene Region," *Journal of Virology* 63(6):2699–2708, 1989.

Stenberg, "The Human Cytomegalovirus Major Immediate–Early Gene," *Intervirology* 39:343–349, 1996.

Stinski and Roehr, "Activation of the Major Immediate Early Gene of Human Cytomegalovirus by cis–Acting Elements in the Promoter–Regulatory Sequenece and by Virus–Specific trans–Acting Components," *Journal of Virology* 55(2):431–441, 1985.

Thrower et al., "Regulation of a Human Cytomegalovirus Immediate–Early Gene (US3) by a Silencer–Enhancer Combination," *Journal of Virology* 70(1):91–100, 1996.

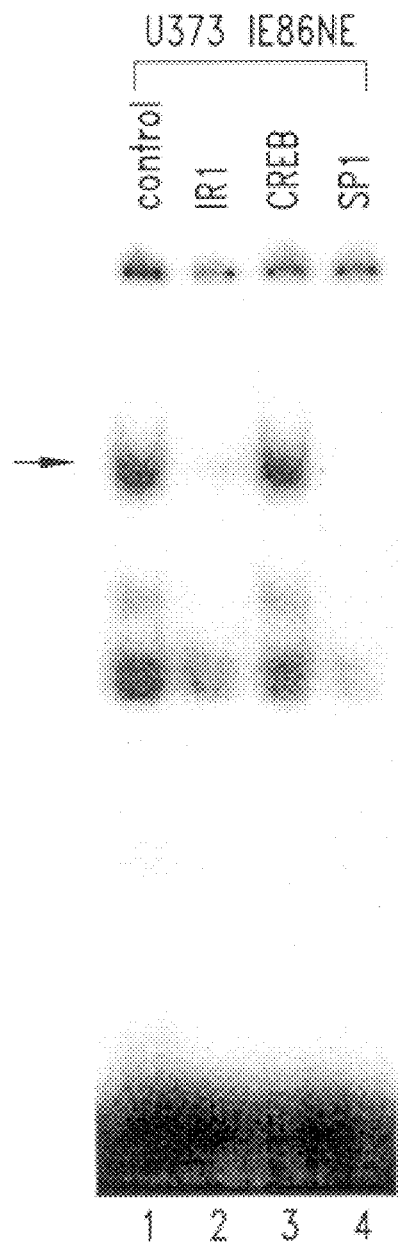
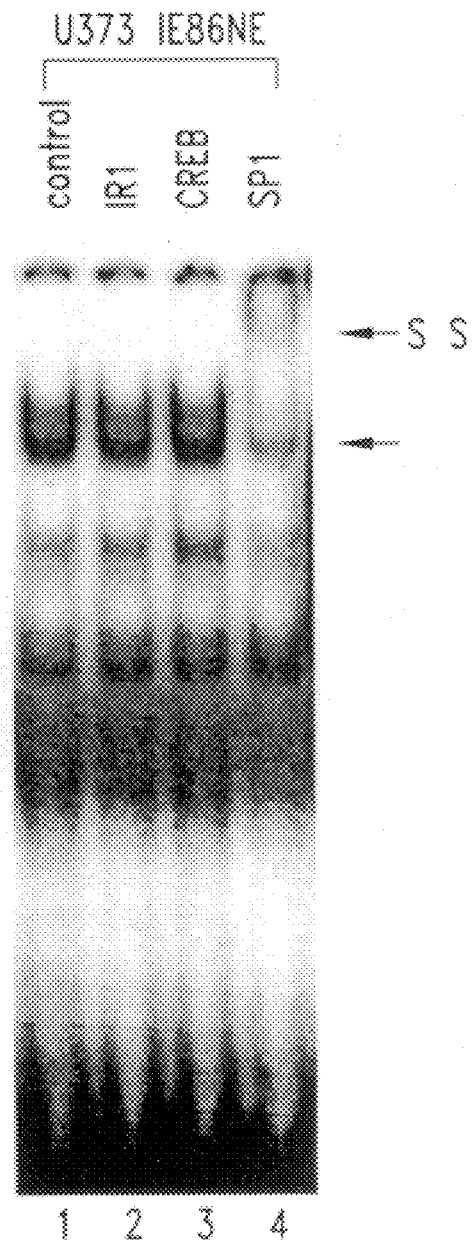
Fig. 10A
Fig. 10B

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (xi) SEQUENCE DESCRIPTION: SEQ ID NO:1:

CCCAAGCTTG GGGGAATTCA ACTCGTACAA GCAG      34

(2) INFORMATION FOR SEQ ID NO:2:

(i) SEQUENCE CHARACTERISTICS:
      (A) LENGTH: 30 base pairs (B) TYPE: nucleic acid
            (C) STRANDEDNESS: single
            (D) TOPOLOGY: linear (xi) SEQUENCE DESCRIPTION: SEQ ID NO:2:

CCCAAGCTTG GGTCAGACGA CGGTGGTCCC                                    30

(2) INFORMATION FOR SEQ ID NO:3:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:3:

CGGGGTACCC CGCACAGAGG TAACAAC                                       27

(2) INFORMATION FOR SEQ ID NO:4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:4:

GAAGATCTTC GGCGGTGGAG CGAGTGC                                       27

(2) INFORMATION FOR SEQ ID NO:5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:5:

GTTACAGGCT CCGCCTTC                                                 18

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:6:

GGAAGGCGGA GCCTGTA                                                  17

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:7:

GTTACAGATA TCGCCTTC                                                 18

(2) INFORMATION FOR SEQ ID NO:8:

(i) SEQUENCE CHARACTERISTICS:
            (A) LENGTH: 17 base pairs
            (B) TYPE: nucleic acid
            (C) STRANDEDNESS: single (D) TOPOLOGY: linear (xi) SEQUENCE DESCRIPTION: SEQ ID NO:8:

GGAAGGCGAT ATCTGTA                                                          17

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:9:

CGTTTAGTGA ACCGTCAGAT                                                       20

(2) INFORMATION FOR SEQ ID NO:10:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:10:

TCTGACGGTT CACTAAACG                                                        19

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:11:

GCGGCGGTGA ACCGTCAGAT                                                       20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:12:

TCTGACGGTT CACCGCCGCC                                                       20

(2) INFORMATION FOR SEQ ID NO:13:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:13:

TAGCGTTGCG ATTTGCAGTC CGCTCC                                                26

(2) INFORMATION FOR SEQ ID NO:14:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:14:

GGAGCGGACT GCAAATCGCA ACGCT                                      25

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:15:

TAGCGTTGTA ACCCATAGTC CGCTCC                                     26

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

GGAGCGGACT ATGGGTTACA ACGCT                                      25

METHOD FOR IDENTIFYING AGENTS THAT MODULATE TRANSCRIPTION OF HUMAN CYTOMEGALOVIRUS POLYMERASE

CROSS-REFERENCE TO RELATED APPLICATION

This application is a continuation-in-part of U.S. patent application Ser. No. 08/720,543, filed Sep. 30, 1996.

TECHNICAL FIELD

The present invention relates generally to human cytomegalovirus infection. The invention is more particularly related to the identification of proteins and other agents that modulate gene expression necessary for HCMV replication and to the use of such agents in antiviral therapies.

BACKGROUND OF THE INVENTION

Human cytomegalovirus (HCMV) is a ubiquitous member of the herpesvirus family that can induce a wide range of diseases, typically in newborns and immunocompromised adults. Nearly one percent of all live births in the United States are associated with congenital HCMV infection, with approximately 5 to 10 percent of infections resulting in significant neurological defects. In bone marrow transplant recipients, mortality due to HCMV pneumonia can be as high as forty percent. In addition, disseminated HCMV infection is common in AIDS patients and is frequently associated with conditions such as gastroenteritis and sight-threatening chorioretinitis.

The viral genome consists of a large double-stranded DNA molecule of approximately 230 kilobase pairs packaged within an enveloped capsid to form the infectious virion. Productive infection is species- and cell-specific and requires the tightly coordinated sequential expression of viral genes. Viral genes are divided into three kinetic classes: immediate early (IE), early (E) and late (L). The IE gene products, regulated by a complex enhancer promoter, are synthesized immediately after entry of the viral genome into the nucleus of infected cells and rely primarily on host factors for their expression. Transcriptional regulation of IE genes has been extensively studied and three major IE proteins have been characterized: IE72, IE86 and IE55. Early genes are transcribed prior to viral DNA replication. The late genes, which constitute the majority of the viral genome, are transcribed in abundance only after viral DNA replication. Both early and late gene expression is modulated by one or more viral IE proteins, as well as host proteins.

Studies of the biological and biochemical function of IE72, IE86 and IE55 have indicated that these proteins play a critical role in HCMV cascade gene expression. All of these proteins have been shown to be involved in the transactivation of HCMV early promoters, as well as heterologous viral and cellular promoters. IE86 also plays a major role in repressing its own promoter, the major immediate early promoter (MIEP). The IE72 and IE55 proteins act to enhance the activity of the MIEP and augment the stimulatory effect of the IE86 protein on its responsive promoters.

Recently, the IE86 protein was shown to enhance UL112 early promoter activity by binding to discrete sequences. Three IE86 binding sites were identified in this promoter. However, direct binding of IE86 to the promoter is not absolutely required because deletion of these target sites retained 40% of the response to IE86 transactivation (Arlt et al., *J. Virol.* 68:4117–4125, 1994). This transactivation by IE86 appears to involve the interaction of IE86 with the cellular transcriptional factor CREB (Lang et al., *J. Virol.* 69:6030–6037, 1995), which differs from the mechanism of transactivation of the HCMV early promoter UL54 (DNA polymerase, pol). An expression construct encoding the major IE proteins IE72, IE86 and IE55 has been shown to induce transactivation of the pol promoter (see Stenberg et al., *J. Virol.* 64:1556–1665, 1990). However, no IE86 binding sequences have been identified in the promoter. In addition, while HCMV-infected human foreskin fibroblasts showed a DNA binding activity specific for a pol promoter element termed IR1 (see Kerry et al., *J. Virol.* 68:4167–76, 1994), it is unclear which IE protein plays the central role in IR1 DNA binding activity.

While these and other studies have provided basic information about IE protein function, a greater understanding of the temporal cascade of viral gene expression is required in order to identify suitable targets for drug development. In particular, the identification of cell permissivity factors that are required for productive infection of host cells would provide a basis for the development of new therapeutic drugs. Such drugs are urgently needed for treatment of HCMV strains that are resistant to current therapies, which employ viral polymerase nucleoside analog inhibitors.

Accordingly, there is a need in the art for new therapies for HCMV infection targeting viral molecules necessary for the progression of the viral life cycle. The present invention fulfills these needs and further provides other related advantages.

SUMMARY OF THE INVENTION

Briefly stated, the present invention provides antiviral agents that modulate HCMV pol transactivation. In one aspect, the present invention provides methods for identifying an agent that modulates transcription of HCMV DNA polymerase, comprising: (a) transfecting a permissive or nonpermissive cell expressing IE86 and a reporter gene, wherein the reporter gene is under the control of the HCMV DNA polymerase promoter, with a polynucleotide encoding a candidate agent; and (b) evaluating the effect of the candidate agent on reporter gene transcription.

In related aspects, methods for identifying an agent that modulates transcription of HCMV DNA polymerase are provided, comprising: (a) contacting a permissive or nonpermissive cell expressing IE86 and a reporter gene, wherein the reporter gene is under the control of the HCMV DNA polymerase promoter, with a candidate agent; and (b) evaluating the effect of the candidate agent on reporter gene transcription.

Within further aspects, the present invention provides methods for identifying an agent that modulates transcription of HCMV DNA polymerase, comprising: (a) contacting a nuclear extract prepared from permissive or nonpermissive cells expressing IE86 with an oligonucleotide comprising an IR1 element and a candidate agent; and (b) evaluating the effect of the candidate agent on Sp1 binding to the oligonucleotide.

In further aspects, modulating agents that inhibit transactivation of HCMV DNA polymerase by IE86 in permissive cells are provided.

In other aspects, methods for treating HCMV infection in a patient are provided. Such methods may comprise administering to a patient an agent that inhibits transactivation of HCMV DNA polymerase by IE86 in permissive cells. Alternatively, such methods may comprise administering to a patient a polynucleotide encoding an agent that inhibits transactivation of HCMV DNA polymerase by IE86 in permissive cells. Within certain embodiments, an agent inhibits Sp1 binding to an IR1 element is administered.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1A is a graph depicting the level of luciferase activity in U373MG cells cotransfected with Pol-luciferase reporter and increasing amounts of IE72, IE86 or IE55 expression vectors (as indicated), along with a LacZ gene expression vector. Luciferase activity was normalized to the beta-galactosidase activity. FIG. 1B is a histogram showing the fold activation of pol-luciferase by increasing amounts of IE86 or pSVH (which expresses proteins from the major IE gene region). FIG. 1C is an autoradiogram showing the level of IE86 in U373 cells transfected with increasing amounts of IE86 expression vector, as indicated. FIG. 1D is an autoradiogram showing the level of IE86, IE72 and IE55 in U373 cells transfected with increasing amounts of pSVH expression vector, as indicated. Arrows indicate the location of the different IE proteins.

FIG. 5A is a histogram showing the level of luciferase activity in U373MG cells (expressing and not expressing IE86) transfected with increasing amounts of pol-luciferase. FIG. 5C is an autoradiogram depicting the level of IE86 expressed by the stably-transfected U373MG cell line, as determined by Western blot analysis using MAB810 specific for the HCMV IE proteins. FIG. 5B shows the level of luciferase activity in HeLa cells (expressing and not expressing IE86) transfected with increasing amounts of pol-luciferase. FIG. 5D is an autoradiogram showing the level of IE86 expressed by the stably-transfected HeLa cell line, as determined by Western blot analysis.

FIG. 6A is a histogram showing the level of luciferase activity in U373MG cells (expressing and not expressing IE86) transfected with increasing amounts of UL112-luciferase. FIG. 6C is an autoradiogram depicting the level of IE86 expressed by the stably-transfected U373MG cell line, as determined by Western blot analysis using MAB810 specific for the HCMV IE proteins. FIG. 6B shows the level of luciferase activity in HeLa cells (expressing and not expressing IE86) transfected with increasing amounts of UL112-luciferase. FIG. 6D is an autoradiogram showing the level of IE86 expressed by the stably-transfected HeLa cell line, as determined by Western blot analysis.

FIG. 7A shows the results for U373MG cells, where lane 1 shows the control (no extract added), lane 2 shows the binding in the absence of IE86 and lane 3 shows the binding in extract prepared from cells expressing IE86. The location of the specific complex is indicated with the arrow and nonspecific complexes are also shown. FIG. 7B shows the results for HeLa cells, where lane 1 shows the control (no extract added), lane 2 shows the binding in the absence of IE86 and lane 3 shows the binding in an extract prepared from cells expressing IE86. FIG. 7C shows the results of a competition experiment performed using an extract from U373MG cells expressing IE86. In lane 1, only labeled IR1 element is added. In lane 2, a 50-fold excess of unlabeled IR1 is also added, and lane 3 shows the binding in the presence of 50-fold excess of unlabeled mutant IR1. The location of the specific complex is indicated with the arrow.

In FIG. 8A, lane 1 shows the control (no antibody added), lane 2 shows the binding in the presence of MAB810 antibody, and lanes 3 and 4 show the binding in the presence of polyclonal antibodies p65Ab and p50Ab, respectively. FIGS. 8B–8D depict the results of Western blot analyses performed following electrophoretic mobility shift assays. In FIG. 8B, the shifted bands were blotted onto DEAE membrane, and in FIGS. 8C and 8D, the bands were blotted onto nitrocellulose. Membranes were probed with monoclonal antibody specific for IE86. In FIGS. 8B–8D, lane 1 shows the results in the absence of IE86, and lane 2 shows the complex (indicated by the arrow) formed in the presence of IE86. In FIG. 8D, lane 3 shows the results in the absence of IR1 and lane 4 shows the signal obtained using recombinant IE86.

FIGS. 10A and 10B are autoradiograms depicting the results of electrophoretic mobility shift assays performed in the presence and absence of competitor oligonucleotides or specific antibodies. In each case, nuclear extracts prepared from U373MG cells expressing IE86 were incubated with radiolabeled IR1 oligonucleotide. In lane 1 (control) of FIGS. 10A and 10B, complex formation (indicated by the arrow) is shown in the absence of competitor. In FIG. 10A, lanes 2–4 show the effect of adding a 50-fold excess unlabeled IR1, CREB or Sp1 competitor, as indicated. In FIG. 10B, the effect of adding 1 μg of polyclonal antibodies specific for ATF, CREB or Sp1 is shown in lanes 2–4, as indicated. The location of supershifted complex is indicated by SS.

In FIG. 11A, nuclear extracts prepared from U373MG cells (lane 2), U373MG cells expressing IE86 (lane 3), HeLa cells (lane 5) or HeLa cells expressing IE86 (lane 6) were incubated with radiolabeled Sp1 consensus oligonucleotide. Control lanes (1 and 4) show the signal detected in the absence of extract. The location of complex is shown with the arrow. In FIG. 11B, U373MG nuclear extracts were incubated with the same Sp1 probe and 50-fold excess of different unlabeled oligonucleotides (IR1, CREB or Sp1 in lanes 2–4) or polyclonal antibodies (against ATF, CREB or Sp1 in lanes 5–7) as indicated. Arrows indicate Sp1 DNA binding; SS indicates supershifted complex.

DETAILED DESCRIPTION OF THE INVENTION

Figure 1A:
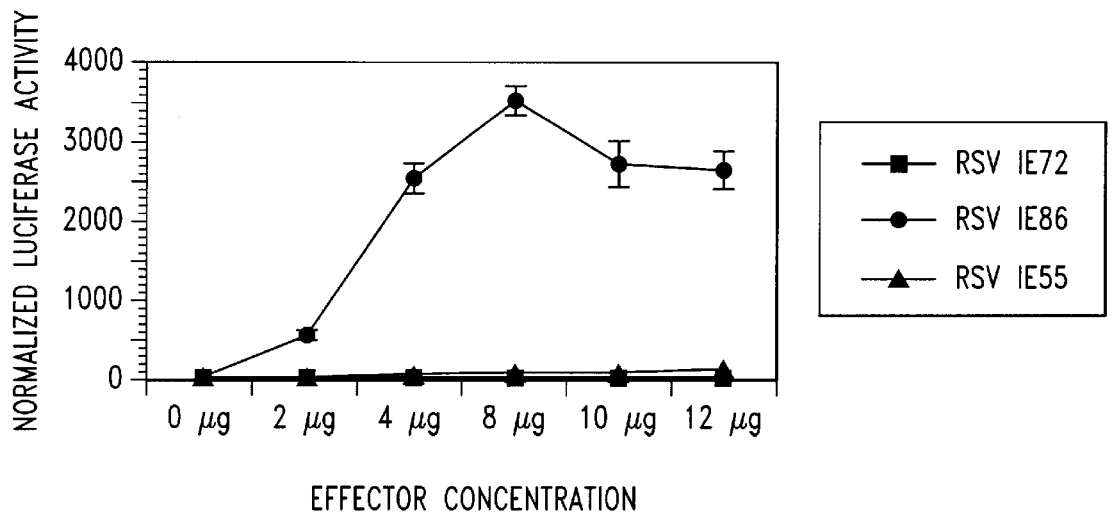
FIGS. 1A–1D illustrate the activation of the HCMV pol promoter by IE86.

As noted above, the present invention is generally directed to proteins and other agents for use in the treatment of HCMV infection. In particular, the present invention is directed to methods for identifying and purifying agents that modulate IE86 transactivation of HCMV DNA polymerase (UL54, pol) in permissive and nonpermissive cells. The present invention is also directed to compositions comprising such agents, which may be used in the treatment of patients infected with HCMV.

It has been found, within the context of the present invention, that IE86 is the major IE protein responsible for transactivation of pol (see FIGS. 1A–1D). Transfection of permissive cells containing the pot promoter with a construct containing IE86 cDNA under the control of a heterologous promoter (e.g. Rous Sarcoma Virus promoter) is generally sufficient for pot promoter transactivation. In contrast, similar constructs containing IE72 or IE55 cDNA do not transactivate pol, and cotransfection of IE86 with IE72 and/or IE55 expression constructs shows no significant activation over the levels observed in the presence of IE86 alone.

Surprisingly, it has also been found within the context of the present invention, that activation of the pol promoter by IE86 is cell type-specific. In other words, while IE86 transactivates the early promoter UL112 in both permissive cells and nonpermissive cells, IE86 transactivates pol only in permissive cells (see FIGS. 2A–2C and 3A–3D). As used herein, "permissive cells" are cells that support HCMV infection (as indicated by sequential viral gene expression and viral production), such as U373MG glial cells, macrophages, human foreskin, embryonic primary or immortalized fibroblasts, bone marrow stem cells, endometrial stromal cells and/or brain endothelial cells. "Nonpermissive" cells are cells in which sequential viral gene expression and viral production do not occur, or cells which HCMV is unable to infect for known or unknown reasons, and include HeLa and C33-A epithelial cells. The transactivation of pot is mediated by the IR1 element, which is specifically bound by a complex containing IE86 in permissive cells (see FIGS. 4A–4B and 5A–5C). The IR1 element has been described by Kerry et al., *J. Virol.* 68:4167–4176, 1994.

It has also been found, within the context of the present invention, that an IR1-bound protein is cellular transcription factor Sp1 (see Kadonaga et al., *Cell* 51:1079–90, 1987), and that the DNA-binding ability of Sp1 is higher in permissive cells than in nonpermissive cells. Cellular factor (s) present in nonpermissive cells inhibit the IE86-mediated Sp1 DNA binding activity. Thus, the present invention is also based on the discovery that IE86-induced functional modulation of cellular transcription factor Sp1 can influence pol gene expression.

Analysis of pol promoter activation may generally be performed as described herein. Briefly, expression constructs containing IE86, IE72 and/or IE55 cDNA may generally be prepared and used to transfect cells as described in Baracchini et al., *Virol.* 188:518–529, 1992 and Depto and Stenberg, *J. Virol.* 63:1232–1238, 1989. The level of pol transactivation may generally be determined using, for example, a PCR-amplified pol promoter region controlling expression of a reporter gene (e.g., luciferase). A HCMV pol promoter region may be amplified from HCMV nucleic acid obtained from any of a variety of sources (such as Advanced Biotechnologies, Inc., Columbia, Md.) using primers derived from the sequence (−425 to +15; see Stenberg, "Sequence-specific activation of CMV early promoters," in E.- S. Huang (ed.), Molecular aspects of human cytomegalovirus diseases 2:350, Springer-Verlag (Berlin, 1993) and methods well known to those of ordinary skill in the art. A reporter gene may be placed under the control of the pol promoter using, for example, any of a variety of commercially available vectors (such as the pGL-2 basic luciferase reporter plasmid, available from Promega, Madison, Wis.) using standard techniques.

As noted above, the present invention is directed to the development of agents that modulate IE86 transactivation of HCMV DNA polymerase. Within the context of the present invention, a "modulating agent" is any compound that is capable of enhancing or, preferably, inhibiting the cell-specific transactivation of pol by IE86. A modulating agent may act directly by interacting with IE86 and/or the pol promoter or by inhibiting expression of IE86. Alternatively, a modulating agent may act indirectly by inhibiting or enhancing the activity of one or more other proteins which, in turn, modulate IE86 transactivation. In particular, a modulating agent may inhibit or enhance IE86-mediated Sp1 DNA binding activity. In general, a modulating agent typically has an $IC_{50}$ of less than 1 μM, and preferably 1–200 nM. Modulating agents may include antibodies (e.g., monoclonal), polynucleotides, endogenous cellular factors and other drugs. Polynucleotides encoding such modulating agents are also encompassed by the present invention.

Modulating agents may be identified using any of a variety of techniques known to those of ordinary skill in the art. For example, to identify an agent that inhibits pol transactivation, a permissive cell containing an expression vector that produces IE86 may be transfected with a reporter gene under the control of the HCMV pol promoter, such that the pol promoter is activated in the absence of modulating agent. Such a cell may then be exposed to a candidate modulating agent under conditions and for a time sufficient to allow the candidate agent to inhibit activation of the pol promoter. Similarly transfected nonpermissive cells may be used to identify agents that enhance pol transactivation or for further study of the function of a candidate agent.

A stable cell line that expresses IE86 may be established using techniques well known to those of ordinary skill in the art. For example, cells may be cotransfected with an expression vector that produces IE86 and a selection plasmid, and transfected cells selected and expanded. Any of a variety of reporter genes known to those of ordinary skill in the art (e.g., the luciferase gene) may be linked to the pol promoter and transfected into such IE86-expressing cells using standard techniques.

Transfected cells may then be exposed to a candidate modulating agent for a suitable amount of time, and the effect of the candidate agent on transactivation may be evaluated by measuring the level and/or activity of the reporter protein. Standard techniques may be employed, such as PCR or hybridization (for evaluating levels of mRNA) or any of a variety of immunoassays or functional assays appropriate for the reporter protein employed. For example, expression of the luciferase (luc) reporter gene may be measured using commercially available assays (obtainable from, e.g., Analytical Luminescence Laboratory, Ann Arbor, Mich.).

Alternatively, endogenous modulating agents may be identified by, for example, using a two-hybrid screen to identify proteins that interact with IE86 or by standard mutagenesis and complementation methods. Such modulating agents may then be purified from cellular extracts based on affinity for IE86 or using other biochemical techniques, using methods well known to those of ordinary skill in the art.

Within other aspects, modulating agents may be identified based on their ability to inhibit or enhance Sp1 binding to an IR1 element. Assays to identify such agents may generally be performed using standard binding assays, such as electrophoretic mobility shift assays. Briefly, a nuclear extract may be prepared from permissive or nonpermissive cells that express IE86 using standard techniques (see Dignam et al., Nucl. Acids Res. 11:1475–89, 1983). An oligonucleotide, preferably double-stranded, comprising an IR1 element may then be added to the extract, with or without the addition of a candidate modulating agent, under conditions that permit binding of Sp1 to the IR1 element. For use in such assays, an IR1 element contains, at minimum, 16 to 18 nucleotides derived from the IR1 element described by Kerry et al., J. Virol. 68:4167–76, 1994. Suitable IR1 element oligonucleotides include the double stranded oligonucleotide formed by annealing the single stranded oligonucleotides 5'-GTTACAGGCTCCGCCTTC (forward; SEQ ID NO: 5) and 5'-GGAAGGCGGAGCCTGTA (reverse; SEQ ID NO: 6). Following incubation with extract, the extent of Sp1 binding to the IR1 element may then be evaluated as described herein. An agent that inhibits Sp1 binding to the IR1 element in extracts prepared from permissive cells inhibits the cell-specific transactivation of pol by IE86. An agent that enhances Sp1 binding to IL1 in extracts prepared from nonpermissive cells enhances IE86-mediated transactivation of pol.

It will be readily apparent to those of ordinary skill in the art that variants of IE86 that retain the ability to transactivate pol may also be employed in the methods described herein. For example, portions of IE86 may be suitable. Specific regions responsible for interaction with cellular factors may be identified using standard deletion mapping techniques, which are well known to those of ordinary skill in the art. In addition, or alternatively, sequences may be added to the N- or C-terminus to aid in the preparation and/or use of the derivative for affinity procedures.

Antibody modulating agents encompassed by the present invention may be polyclonal or monoclonal, and may be specific for IE86 or for another protein involved in IE86 transactivation. Preferred antibodies inhibit IE86 transactivation. Antibodies may be prepared by any of a variety of techniques known to those of ordinary skill in the art (see, e.g., Harlow and Lane, Antibodies: A Laboratory Manual, Cold Spring Harbor Laboratory, 1988). In one such technique, an immunogen comprising IE86 or a portion thereof is initially injected into a suitable animal (e.g., a mouse, rat, rabbit, sheep or goat), preferably according to a predetermined schedule incorporating one or more booster immunizations, and the animal is bled periodically. Polyclonal antibodies specific for IE86 may then be purified from such antisera by, for example, affinity chromatography using IE86 coupled to a suitable solid support.

Monoclonal antibodies specific for IE86 may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with IE86). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Antibodies may then be tested for their ability to function as modulating agents, as described above.

Modulating agents may also be endogenous cellular factors or other proteins. For example, an agent that inhibits pol transactivation may be a protein present in nonpermissive cells. Such modulating agents may generally be identified by transfecting a permissive cell expressing IE86 and a reporter gene under the control of the HCMV DNA polymerase promoter with a polynucleotide encoding a protein present in nonpermissive cells (e.g., CDNA prepared from nonpermissive cells). The effect of the encoded protein on reporter gene transcription may then be evaluated as described above. Endogenous protein modulating agents may be purified by expressing the cDNA in suitable cells and using standard purification techniques.

In another aspect of the present invention, one or more modulating agents as described above may be used to treat a patient infected with HCMV. For administration to a patient, one or more modulating agents are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, antioxidants, chelating agents and/or inert gases, and/or other active ingredients.

Alternatively, a pharmaceutical composition may comprise a polynucleotide encoding a modulating agent, such that the modulating agent is generated in situ, in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–49, 1993.

Various viral vectors that can be used to introduce a nucleic acid sequence into the targeted patient's cells include, but are not limited to, vaccinia or other pox virus, herpesvirus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for modulating agents is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well as doses, will vary from patient to patient. In general, the pharmaceutical compositions may be administered intravenously, intraperitoneally, intramuscularly, subcutaneously, intracavity or transdermally. Typically, between two and three doses may be administered every day for a period of about two weeks. A suitable dose is an amount of a modulating agent or polynucleotide encoding a modulating agent that is sufficient to induce a decrease in the level of infection and/or improvement in the symptoms of a patient afflicted with HCMV infection. Such improvement may be detected by monitoring of viral levels using standard techniques, such as cell based viral assays, PCR and viral culture methods, or through an improvement in clinical symptoms associated with the disease. In general, the amount of polypeptide present in a dose, or produced in situ by DNA present in a dose, ranges from about 0.5 mg to about 250 mg per kg of host, preferably from about 5 mg/kg to about 50 mg/kg. Suitable dose sizes will vary with the size of the patient, but will typically range from about 0.5 mL to about 5 mL for 10–60 kg animal.

The following Examples are offered by way of illustration and not by way of limitation.

EXAMPLES

Example 1

Identification of IE86 as a Major Transactivator of HCMV DNA Polymerase

This Example illustrates IE86-mediated transactivation of the pol promoter.

To identify the transactivating IE protein, it was first determined that the pol promoter construct responded to immediate early proteins as previously reported. The UL54 (Pol) promoter sequence, from position −425 to +15, was amplified by PCR using cosmid pCM1058 (a gift from Peter Ghazal, The Scripps Research Institute, La Jolla, Calif.) as a template. This promoter sequence may also be obtained directly from the HCMV genome. The oligonucleotide primer sequences used were:

5'-CCCAAGCTTGGGGGAATTCAACTCGTACAAGCAG-3' (sense)
(SEQ ID NO:1);

and

5-CCCAAGCTTGGGTCAGACGACGGTGGTCCC-3' (antisense)
(SEQ ID NO:2).

These oligonucleotide primers introduced a HindIII restriction site at the 5' and 3' ends of the UL54 (Pol) promoter fragment allowing insertion into the pGL2-basic luciferase reporter plasmid (Promega, Madison, Wis.). The PCR fidelity of UL54 (Pol) promoter sequence was confirmed by sequencing. Expression vectors for each of the HCMV immediate early proteins, RSV IE72, RSV IE86, RSV IE55 (gifts from Peter Ghazal; see Baracchini et al., *Virol.* 188:518–529, 1992), and pSVH, which expresses proteins from the major IE gene region have been described (Depto et al., *J. Virol.* 63:1232–38, 1989).

U373MG cells were cotransfected with the reporter construct, and with increasing amounts of pSVH and a LacZ gene expression vector (Promega. Madison, Wis.), using the Profection™ mammalian transfection system (Promega, Madison, Wis. Cat# E1200). Forty hours posttransfection, cells were harvested and assayed for luciferase activity as prescribed by the manufacturer (Analytical Luminescence Laboratory, Ann Arbor, Mich.) and for β-gal activity as prescribed by the manufacturer (Promega, Madison, Wis.). Luciferase activity, normalized to the β-gal activity, is presented in FIG. 1A. These results show that cotransfection with pSVH, a construct encoding the three immediate early genes (IE72, IE86 and IE55) from the endogenous genomic fragment under control of its own major immediate early promoter, resulted in strong activation of the pol promoter as measured by expression of the luciferase reporter. Thus, the pol-luciferase reporter construct carries all regulatory elements previously shown to mediate the response to the immediate early proteins expressed from the pSVH expression vector.

Separate transfections were then performed using each of three expression constructs encoding the IE72, IE55 and IE86 cDNA sequences under control of the heterologous Rous Sarcoma Virus promoter. Transfections were performed as described above. Interestingly, only the IE86 expression vector was capable of activating the pol promoter (FIG. 1A). Neither the IE72 nor the IE55 expression vectors yielded significant activation of the pol promoter (FIG. 1A).

Figure 1B:
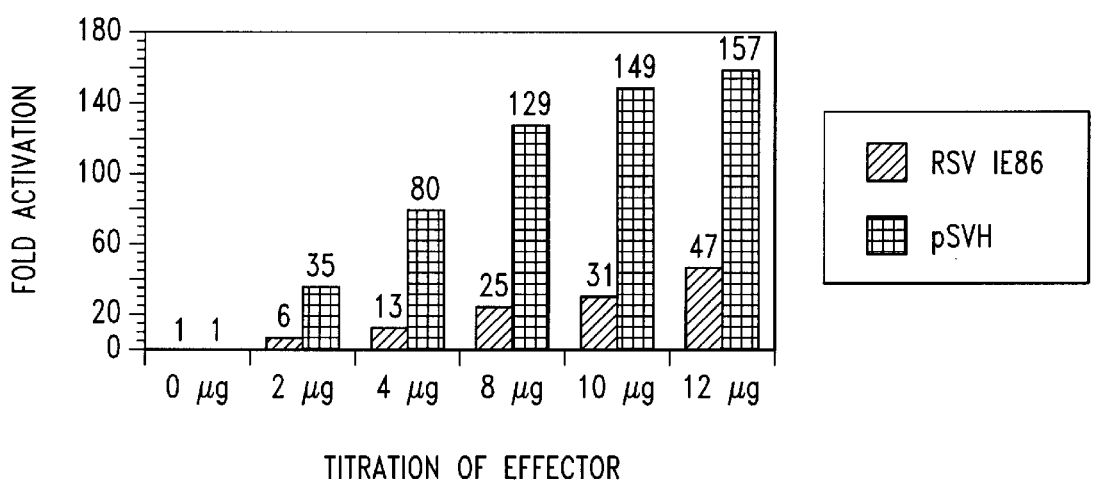

Comparison of pol promoter activation by cotransfection with pSVH and RSVIE86 showed about three-fold stronger effect by the former expression vector (FIG. 1B). Therefore, assays were performed for the level of immediate early protein expression by the different expression vectors using Western analyses. For each sample, 25 μg of total protein were separated by SDS-polyacrylamide electrophoresis and transferred to Hybond™-ECL nitrocellulose membrane (Amersham, Arlington Heights, Ill.). Monoclonal antibody MAB810 against HCMV immediate early proteins (Chemicon, Temecula, Calif.), was used. Proteins bound by primary antibodies were detected with a secondary antibody conjugated with alkaline phosphatase according to the manufacturer's protocol (Amersham, Arlington Heights, Ill.).

Figure 1C:
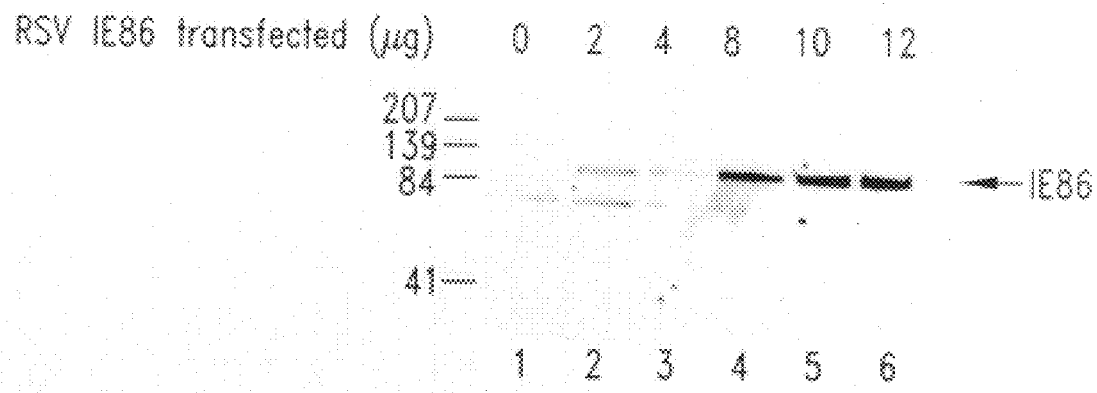
Figure 1D:
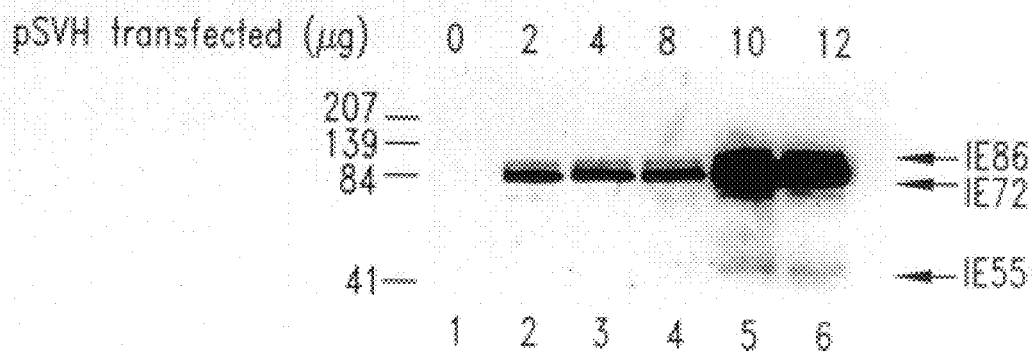

These analyses indicate that IE86 protein levels are higher in cells transfected with the pSVH vector than in cells transfected with RSVIE86 (FIGS. 1C and 1D). In addition, cotransfection of RSVIE86 with RSVIE72 and/or RSVIE55 showed no significant activation over the levels seen in presence of IE86 alone (data not shown). Therefore, the IE86 immediate early protein is the major factor responsible for transactivation of the pol promoter.

Example 2

Cell Type-Specific Activation of the Pol Promoter by IE86

This Example illustrates the ability of IE86 to transactivate the pol promoter in a cell-specific manner.

The response of two early gene promoters, pol and UL112, to IE86 expression in permissive and nonpermissive cells was analyzed. UL112 promoter sequence from −352 to +37 was amplified by PCR using cosmid pCM1058 as a template. The primer sequences for the UL112 promoter were:

5'-CGGGGTACCCCGCACAGAGGTAACAAC-3'    (sense)
(SEQ ID NO:3);

and

5'-GAAGATCTTCGGCGGTGGAGCGAGTGC-3'    (antisense)
(SEQ ID NO:4).

These primers introduced KpnI and BglII restriction sites at the 5' and 3' ends of the UL112 promoter fragment, respectively, allowing directional insertion into the pGL2-basic luciferase reporter plasmid (Promega, Madison, Wis.).

Figure 2A:
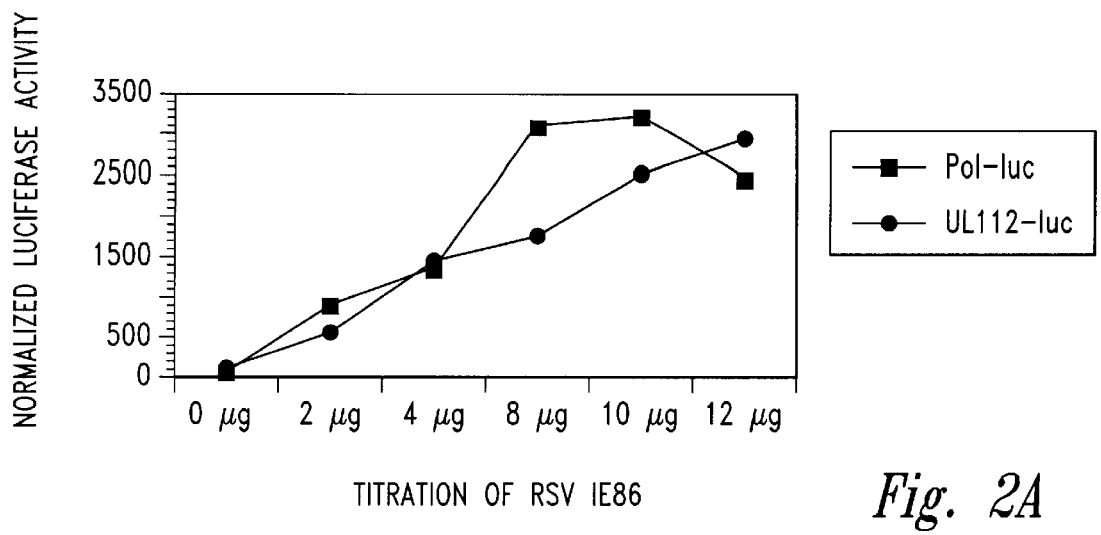
FIGS. 2A–2C are graphs depicting the level of luciferase activity in U373MG cells (FIG. 2A), HeLa cells (FIG. 2B) and C33-A cells (FIG. 2C) cotransfected with pol-luciferase or UL112-luciferase and increasing amounts of RSV IE86, as indicated, and a LacZ gene expression vector. Luciferase activity was normalized to the beta-galactosidase activity.
Figure 2B:
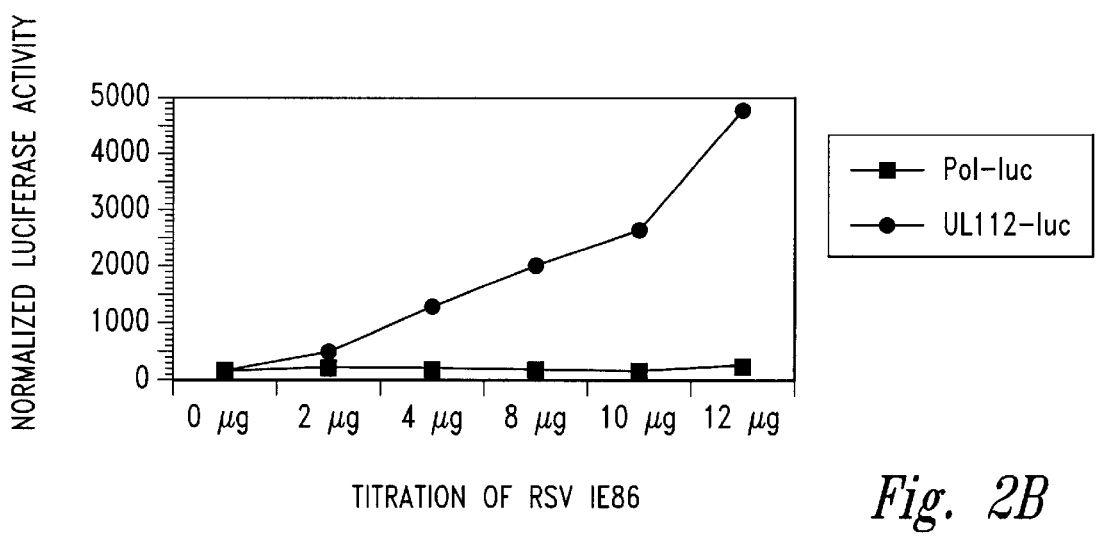
Figure 2C:
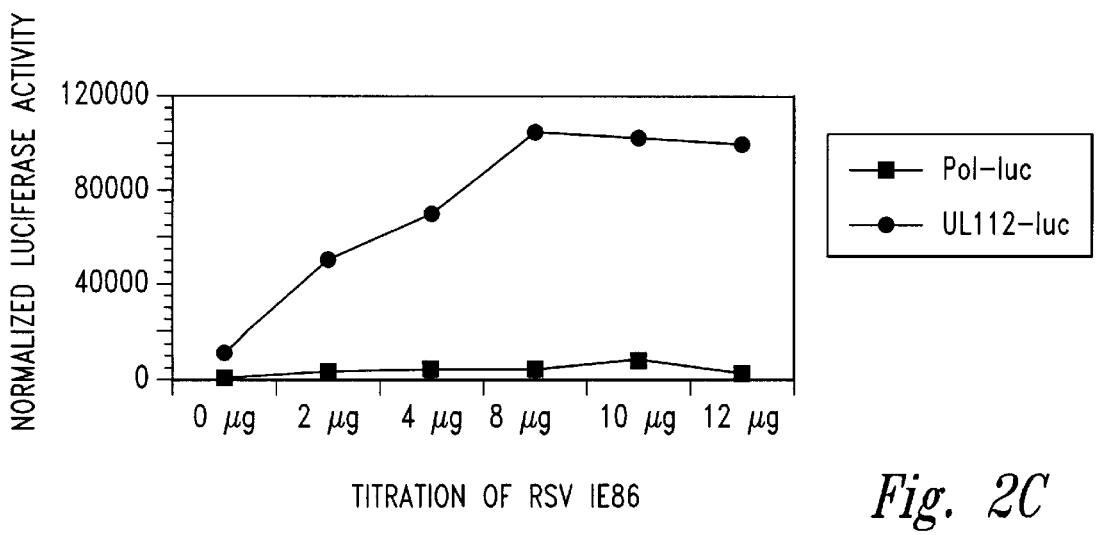

Transfection of U373MG, human foreskin fibroblast (HFF), HeLa and C33-A cells with reporter constructs and increasing amounts of the IE86 construct (RSVIE86) and lacZ expression vector were performed as described above. Luciferase activities normalized to the β-galactosidase activity for U373MG, HeLa and C33-A cells are shown in FIGS. 2A–2C. Luciferase activities for all four cell types are also shown in FIGS. 3A–3D (pol-luc construct) and 4A–4D (UL112-luc construct).

Figure 3A:
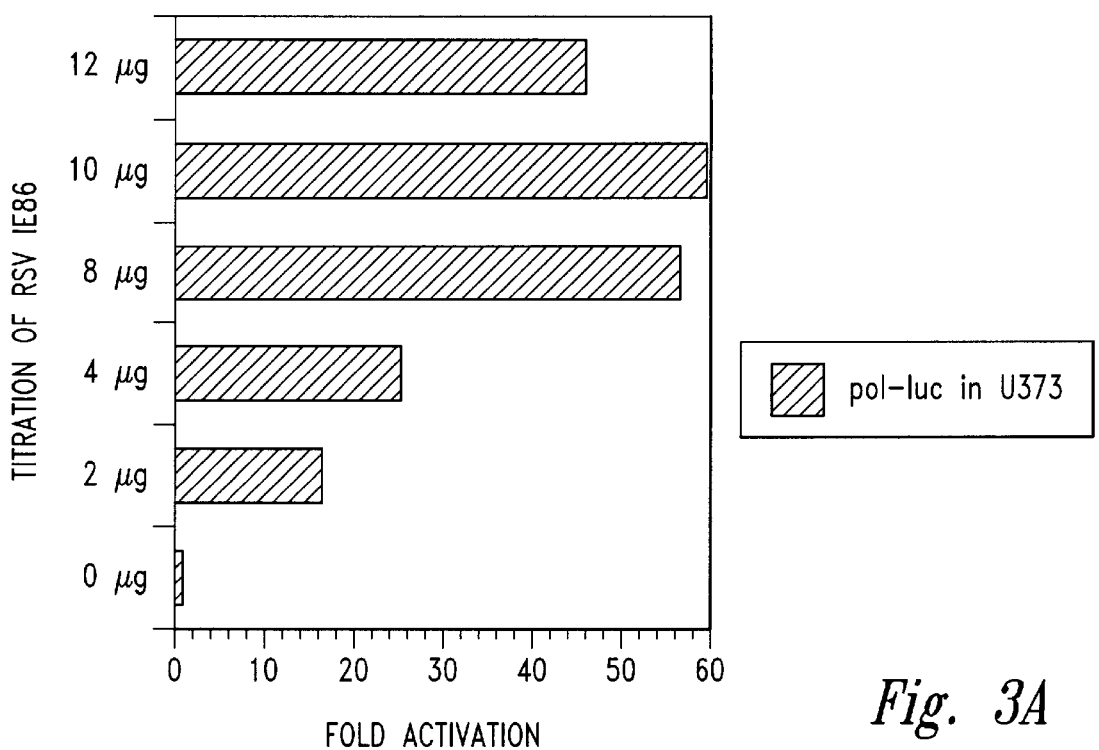
FIGS. 3A–3D are histograms depicting the level of luciferase activity in permissive U373MG (A) and HFF cells (B), and in nonpermissive HeLa (C) and C33-A (D) cells transfected with pol-luciferase and a lacZ gene expression vector and titrated with increasing amounts of RSV IE86, as indicated. Luciferase activities were normalized to β-galactosidase activity. Fold activation is shown. The data represent three independent experiments.
Figure 3B:
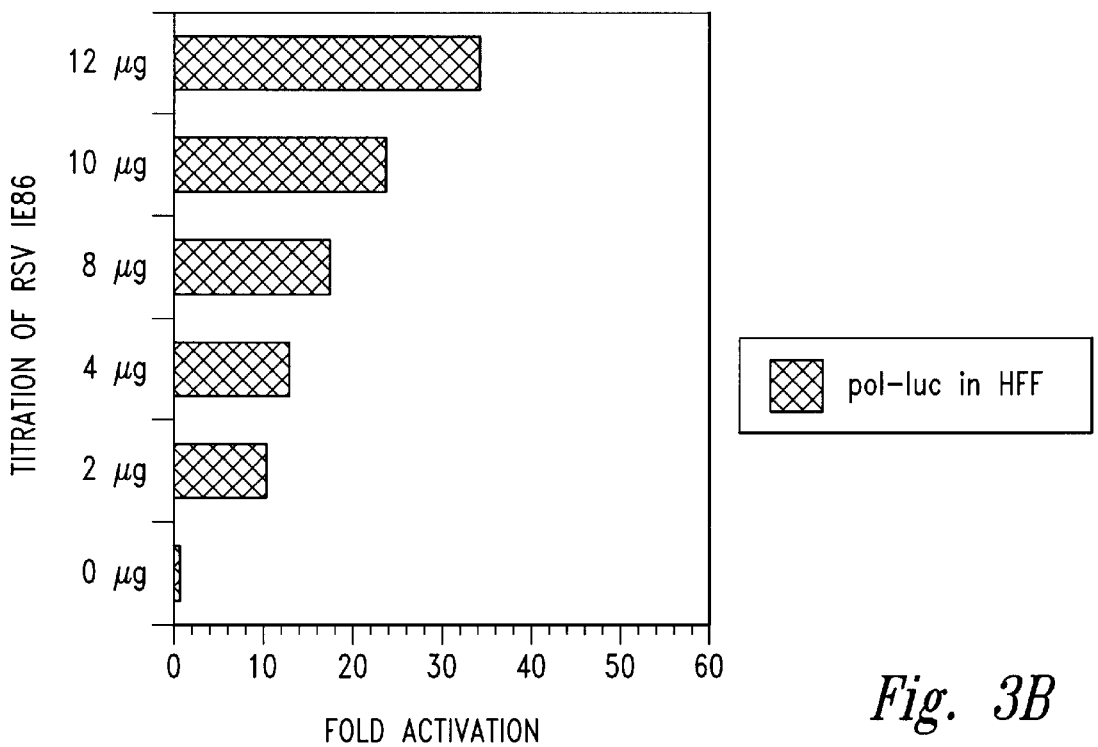
Figure 3C:
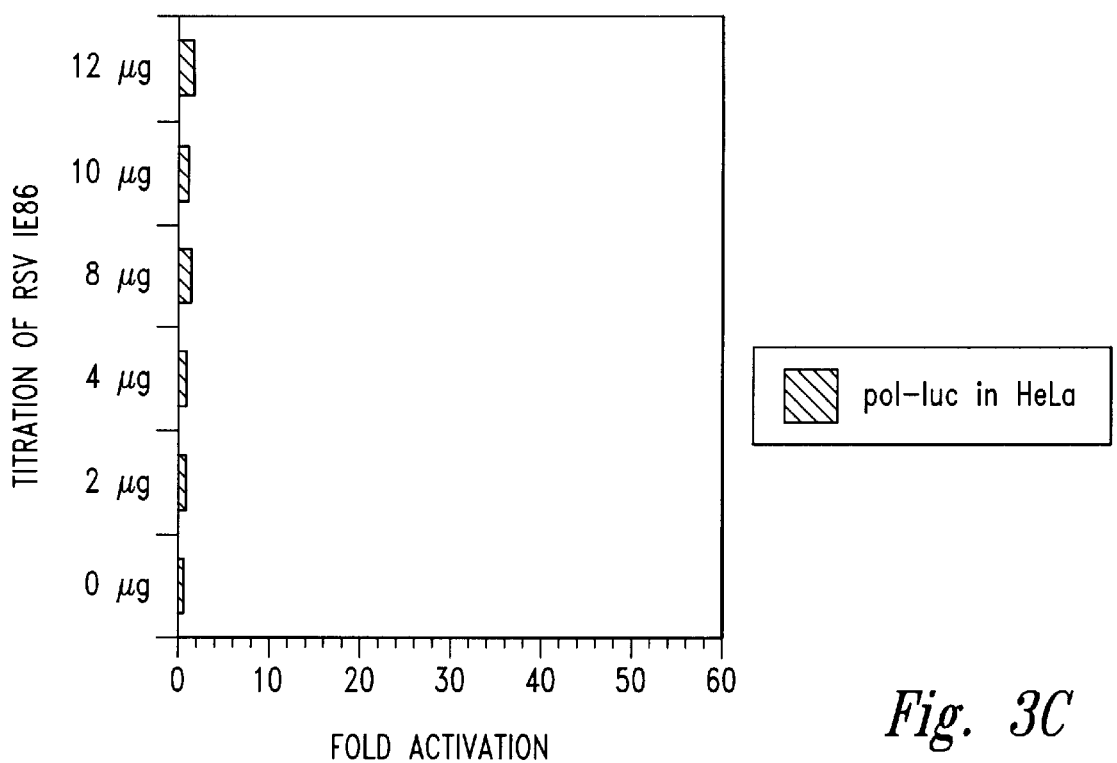
Figure 3D:
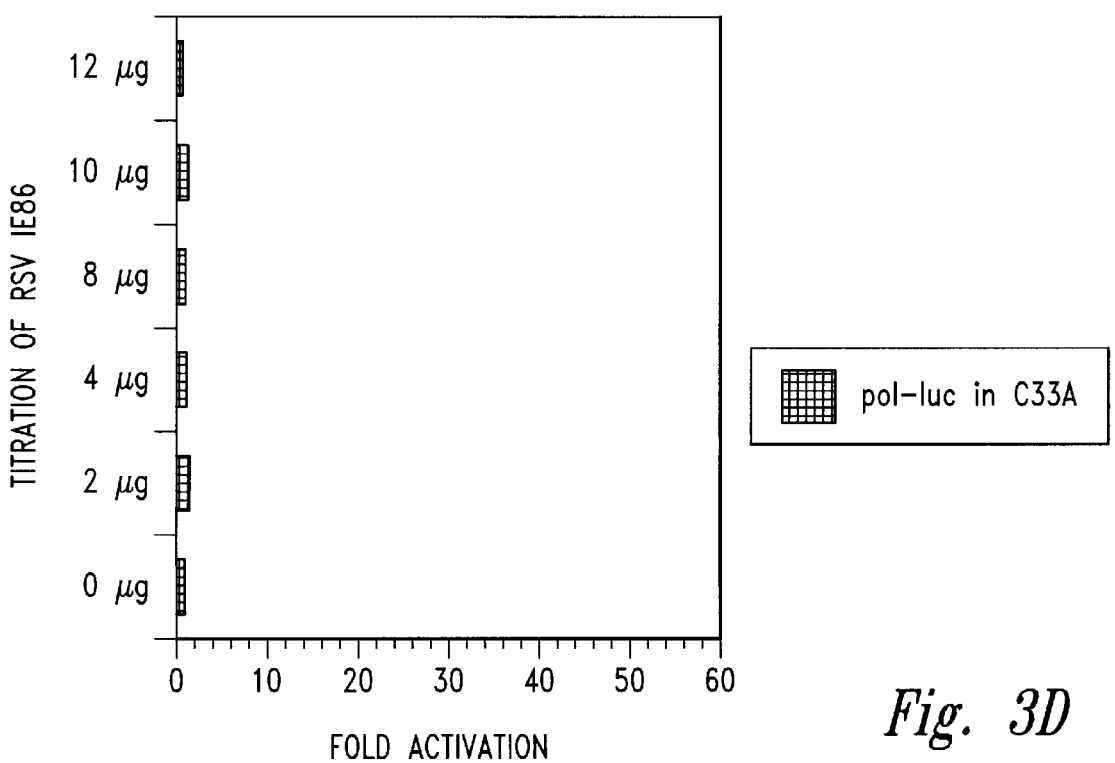
Figure 4A:
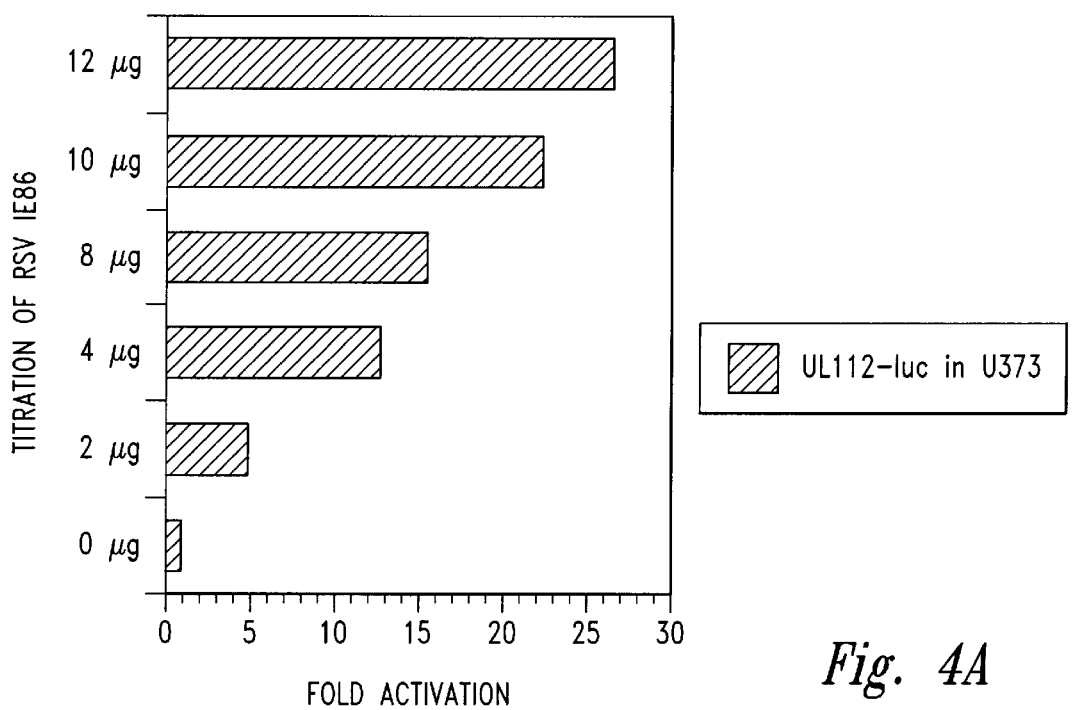
FIG. 4A–4D are histograms depicting the level of luciferase activity in permissive U373MG (A) and HFF cells (B), and in nonpermissive HeLa (C) and C33-A (D) cells transfected with UL112-luciferase and a lacZ gene expression vector and titrated with increasing amounts of RSV IE86, as indicated. Luciferase activities were normalized to β-galactosidase activity. Fold activation is shown. The data represent three independent experiments.
Figure 4B:
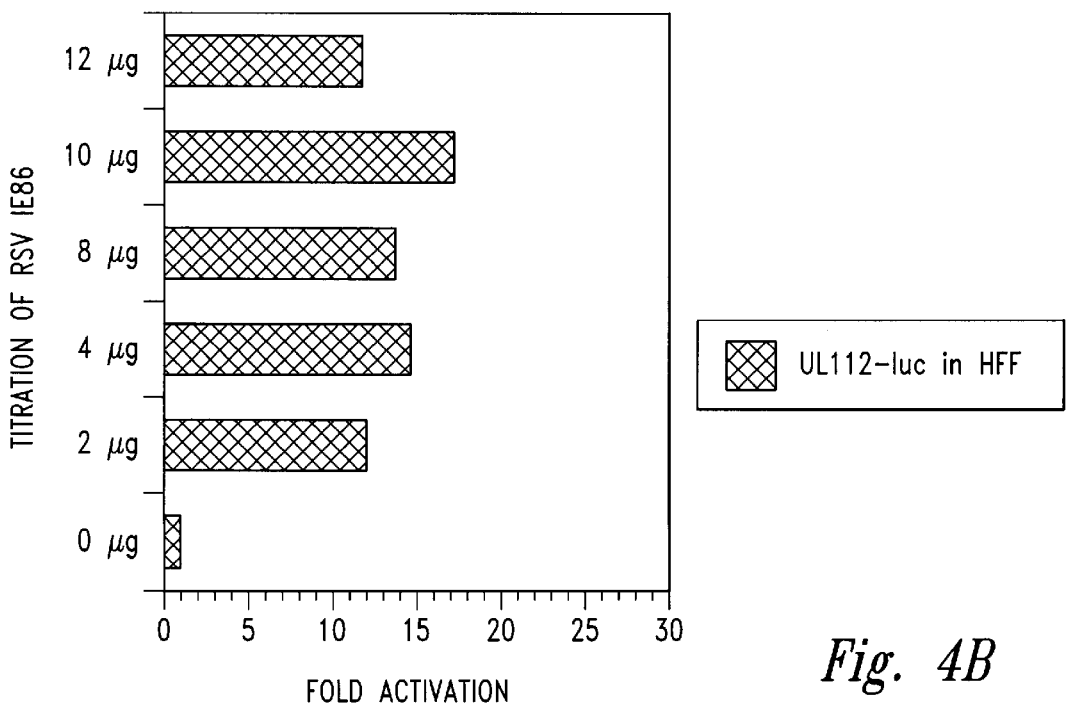
Figure 4C:
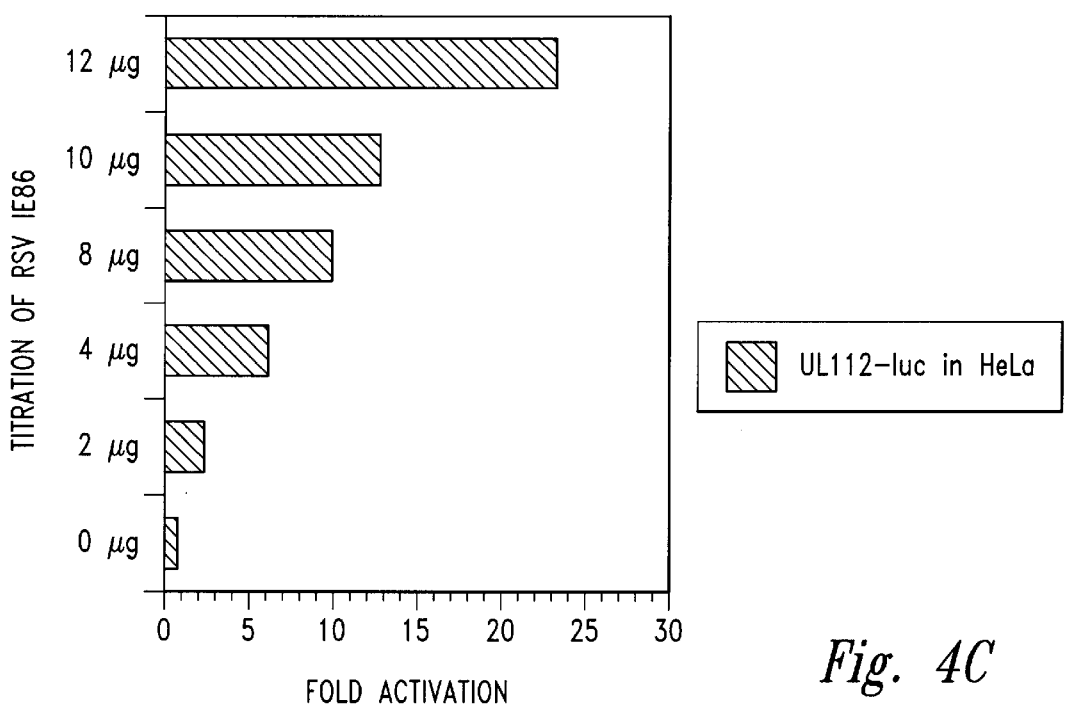
Figure 4D:
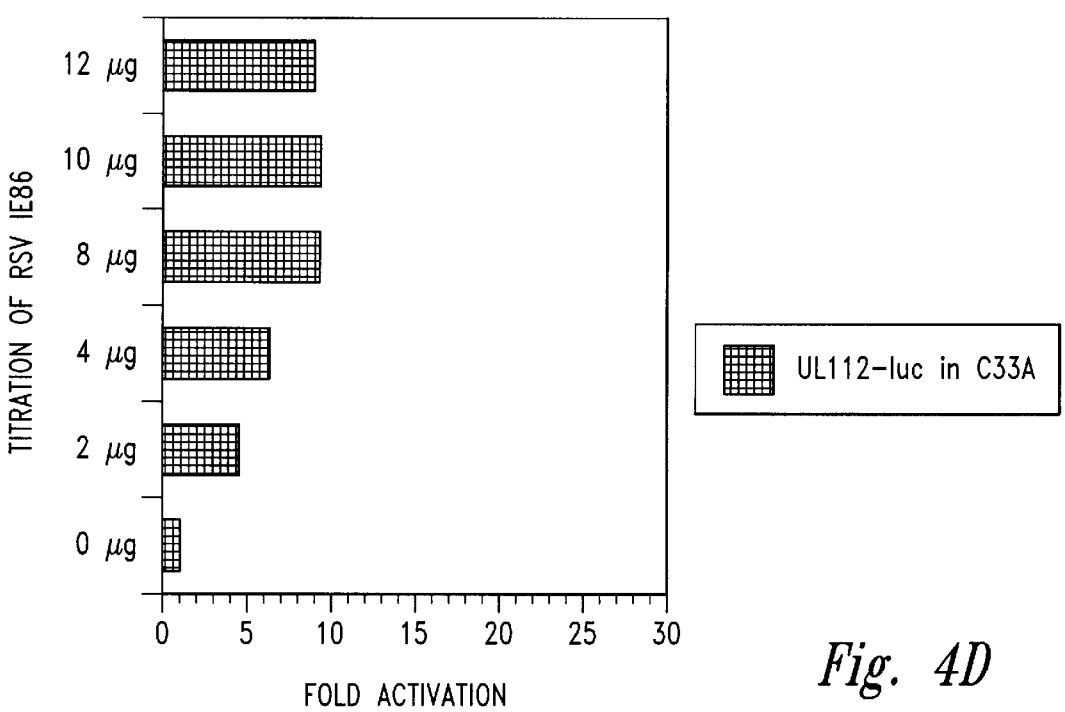

In the permissive U373MG glial cells, both promoters were efficiently activated by cotransfected RSVIE86 (FIGS. 2A, 3A and 4A). The pol promoter in U373MG and HFF cells was transactivated by IE86 60-fold and 35-fold, respectively (FIGS. 3A and 3B), while the UL112 promoter was transactivated by IE86 28-fold and 18-fold, respectively (FIGS. 4A and 4B). However, no activation of the pol promoter was detected in the nonpermissive HeLa or C33-A epithelial cells (FIGS. 2B, 2C, 3B and 3C). In contrast, the UL112 reporter was transactivated in nonpermissive cells by cotransfection with RSVIE86 (FIGS. 2B, 2C, 4B and 4C). The lack of luciferase expression from the pol-luciferase reporter is not simply due to inefficient transfection, since the data shown are normalized for the β-galactosidase levels expressed by a cotransfected control plasmid and the UL112-luciferase reporter was still activated by IE86 in those cells.

To confirm the cell-specific activation, the same reporter plasmids were tested in cell lines stably expressing the IE86 protein. To establish U373MG and HeLa stable cell lines expressing IE86, the RSV IE86 and pSV2Neo (Clontech Laboratories, Inc., Palo Alto, Calif.) selection plasmids were cotransfected into U373MG and HeLa cells by the calcium phosphate method. Transfectants were selected in medium containing 0.6 mg/ml G418 on the third day after transfection. G418-resistant clones were expanded and $3 \times 10^4$ cells seeded in triplicate in a 96 well plate. Cells were harvested and assayed for IE86 by Western blot analysis as described above. Clones showing expression of IE86 protein were amplified and used for further studies.

Figure 5A:
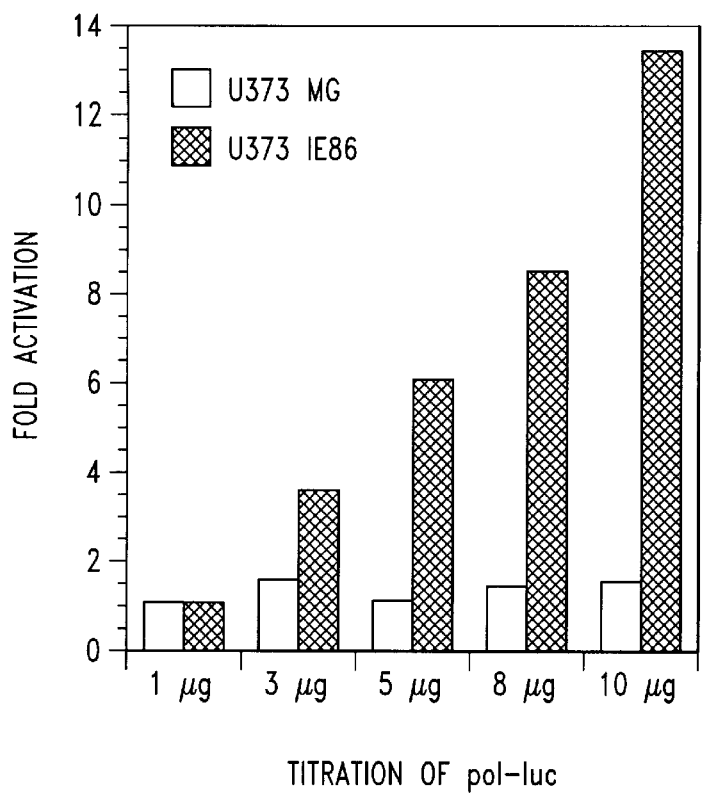
FIGS. 5A–5D are histograms (A and B) and autoradiograms (C and D) depicting the level of early promoter activation in representative permissive and nonpermissive cells stably expressing IE86.
Figure 5B:
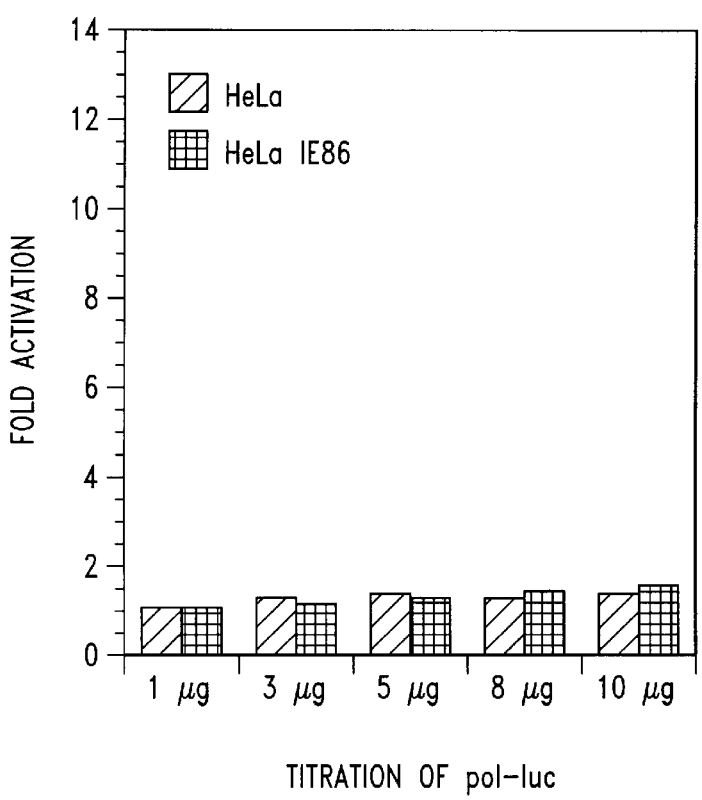
Figure 5C:
Figure 5D:
Figure 6A:
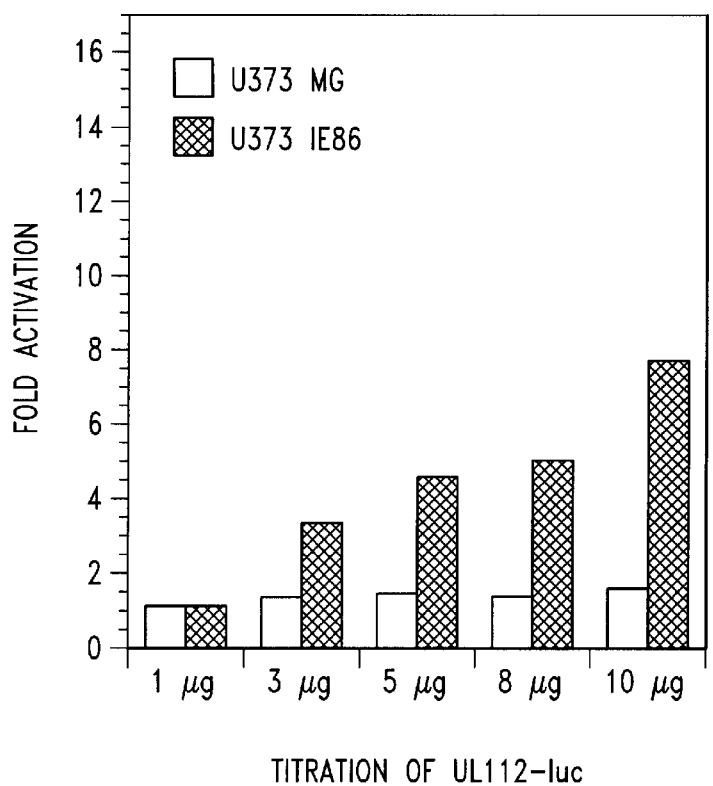
FIGS. 6A–6D are histograms (A and B) and autoradiograms (C and D) depicting the level of UL112 promoter activation in representative permissive and nonpermissive cells stably expressing IE86.
Figure 6B:
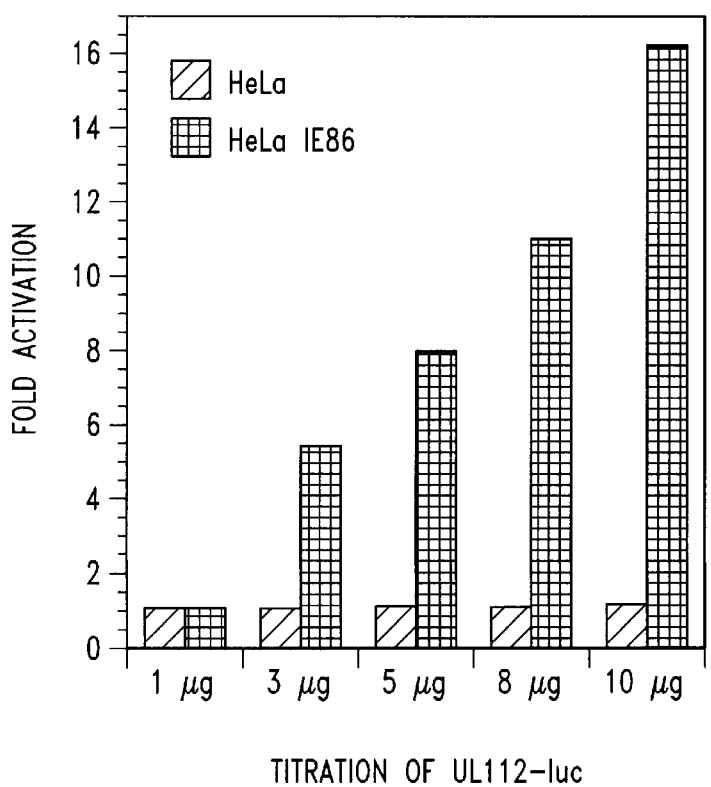
Figure 6C:
Figure 6D:

U373MG and HeLa cell clones constituitively expressing similar amounts of IE86 were then transfected with increasing amounts of the pol-luciferase and UL112-luciferase reporters. Cells were then harvested for the luciferase activities as described above. Although the levels of IE86 protein expressed were identical (as determined by Western blot using MAB810 against the IE proteins as described above), the luciferase reporter protein encoded in the pol promoter plasmid was only expressed in U373MG and not in HeLa cells (FIGS. 5A and 5B). Transfection with the UL112-luciferase reporter plasmid showed significant activation in both U373MG and HeLa cells expressing IE86 protein (FIGS. 6A and 6B). Therefore, IE86 transactivates the pol promoter in a cell specific manner.

Example 3

Identification of a Cell Specific Binding Activity to the Inverted Repeat (IR1) Element This Example illustrates the cell specific binding of a complex containing IE86 to the inverted repeat element (IR1) of the pol promoter reported by Kerry et al., *J. Virol.* 68:4167–4176, 1994.

Electrophoretic mobility shift assays were conducted with radioactively labeled IR1 oligonucleotides and nuclear extracts from IE86-expressing and parental U373MG and HeLa cells. The sequences of the IR1 probe were:

```
5'-GTTACAGGCTCCGCCTTC    (forward; SEQ ID NO:5);

and

5'-GGAAGGCGGAGCCTGTA     (reverse; SEQ ID NO:6),
``` and the probe was generated by annealing the oligonucleotides as described by Kerry et al., *J. Virol.* 68:4167–76, 1994. U373MG, U373 IE86, HeLa, and HeLa IE86 nuclear extracts were prepared by the Dignam procedure (Dignam et al., *Nucl. Acids Res.* 11:1475–89, 1983).

For the gel mobility shift assay, the oligonucleotide containing the IR1 element was labeled at the 5' end with [α-$^{32}$P] ATP. 5 μg of nuclear extracts were incubated with 1 μg of poly(dI:dC) poly(dI:dC) and 10,000 cpm of labeled IR1 oligo for 30 min at room temperature in binding buffer (75 mM NaCl, 15 mM Tris, pH7.5, 1.5 mM EDTA, 1.5 mM DTT, 7.5% glycerol, 0.3% NP-40, 20 μg BSA). A 4% polyacrylamide gel was pre-run in standard 0.25× Tris-borate-EDTA at 150 V for at least 1.5 hrs. Sample reactions were then subjected to polyacrylamide gel electrophoresis. Gels were dried and subjected to autoradiography.

Figure 7A:
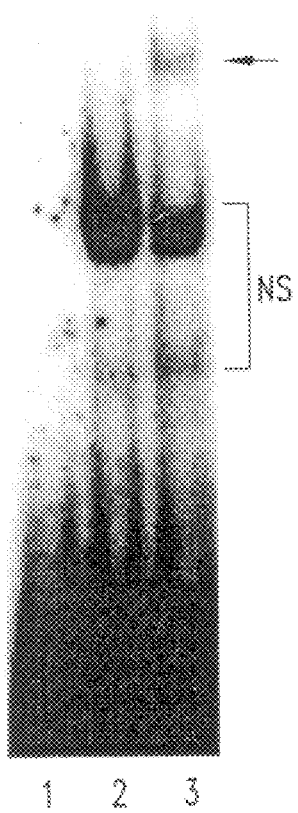
FIGS. 7A–7C are autoradiograms presenting the results of electrophoretic mobility shift assays using the IR1 element and nuclear extracts from IE86-expressing and parental U373MG and HeLa cells.
Figure 7B:
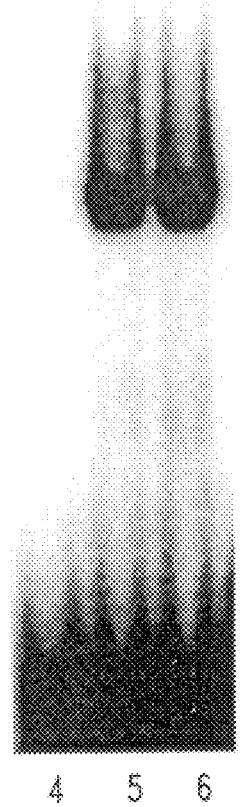

A specific complex was present in IE86-expressing U373MG cells but not in extracts from the parental cell (FIG. 7A). In comparison, HeLa cells did not show the complex in the presence or absence of IE86 (FIG. 7B). The absence of the IE86 specific complex in HeLa cells is not due to a lack or lower level of IE86 protein since, as shown in FIGS. 5 and 6 (C and D), the protein is expressed at similar levels in U373MG cells.

Figure 7C:

The band seen in IE86 expressing U373MG cell extracts was then determined to be specific for the IR1 element. While the wild-type IR1 oligonucleotide (50-fold excess) was able to inhibit the formation of a DNA protein complex containing the radiolabeled IR1 oligonucleotide and factors in the IE86-expressing U373MG cell extracts, a similar amount of oligonucleotide carrying a mutation in the IR1 sequence was not (FIG. 7C). The mutant IR1 oligonucleotide (IRmut) sequences were:

```
5'-GTTACAGATATCGCCTTC    (forward; SEQ ID NO:7)

and

5'-GGAAGGCGATATCTGTA     (reverse; SEQ ID NO:8).
```

Therefore, the DNA complex formed in extracts from U373MG cells expressing the IE86 protein is specific for the IR1 element.

Figures 8A, 8B:
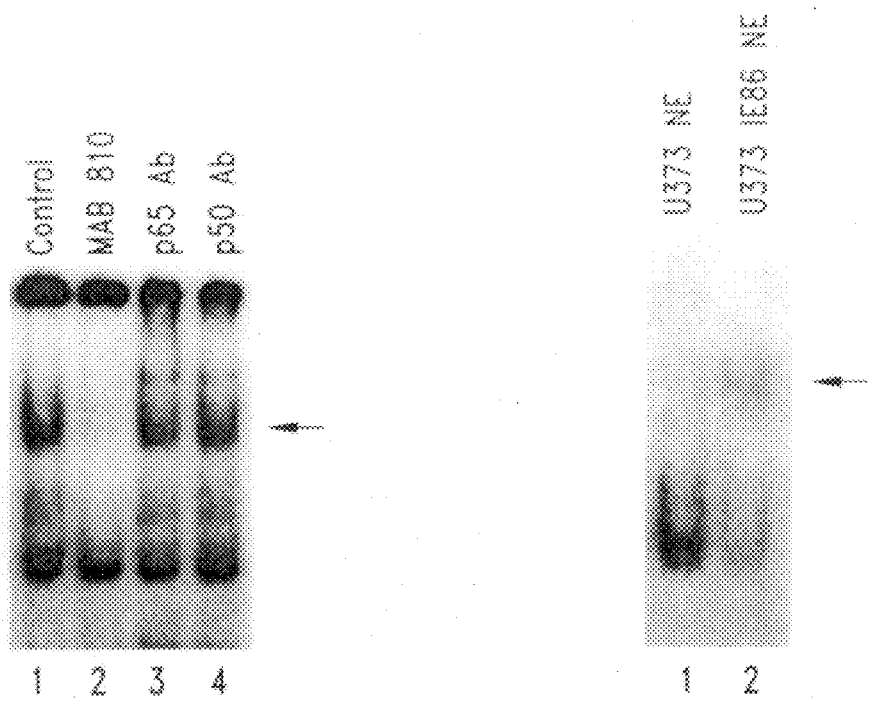
FIGS. 8A–8D are autoradiograms depicting the results of electrophoretic mobility shift assays using nuclear extracts from IE86-expressing U373MG cells and the IR1 element.

To determine whether the IE86 protein itself is part of the complex, the electrophoretic mobility shift assays were repeated with extracts from the IE86 expressing U373MG cells in the absence and presence of different monoclonal antibodies. Antibody super-shift experiments were performed using 1 μg of IE protein-specific monoclonal antibody (MAB810, as described above) or non-specific polyclonal antibodies (p65 and p50 against NFκB; Santa Cruz Biotechnology, Santa Cruz, Calif.). As shown in FIG. 8A, addition of a monoclonal antibody that recognizes IE86 (MAB810) disrupts the IR1 specific complex (lane 2). In contrast, two other monoclonal antibodies specific for the cellular transcription factor NF-κB (p65Ab and p50Ab) had no effect on the IR1 complex (lanes 3 and 4). These results suggest that the viral immediate early protein is present in the specific DNA-binding complex.

Figures 8C, 8D:
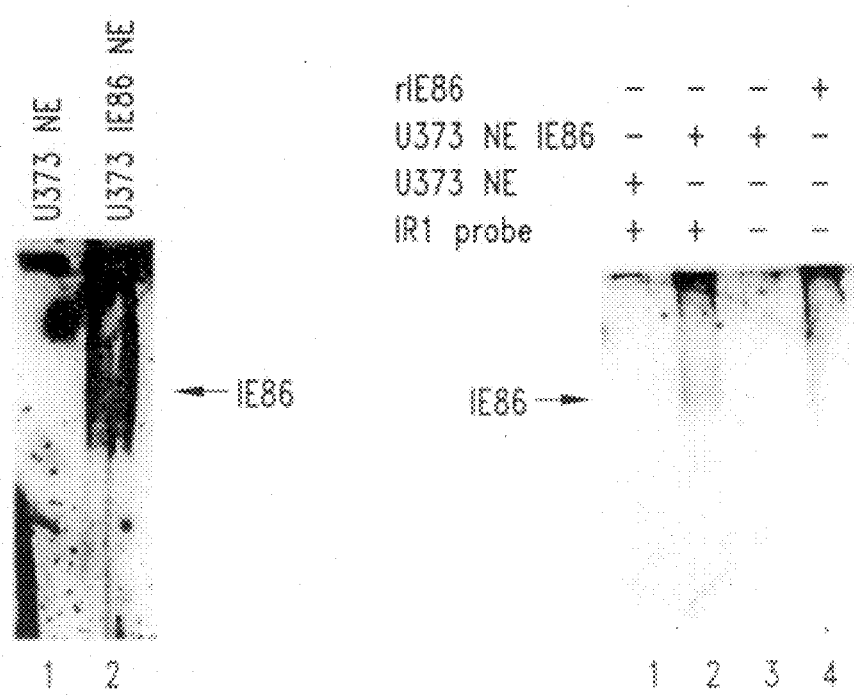

This conclusion is further supported by Western analysis of the shifted band with the IE86 specific monoclonal antibody. As shown in FIGS. 8B and 8C (lane 2), the proteins present in the IR1 complex were efficiently transferred onto DEAE and nitrocellulose membranes, and recognized by IE86-specific antibody. However, this antibody did not detect IE86 protein expressed in U373MG cells or bacteria if IR1 probe was not added to the assay (FIG. 8D, lines 3 and 4), indicating that the band recognized by the IE86-specific antibody represents IE86 protein present in the IR1 complex, and not free IE86 protein. Thus, the data indicate that IE86 is present in the cell-specific complex associated with the IR1 element.

To determine whether IE86 binds to the IR1 element directly or indirectly, a separate electrophoretic mobility shift assay was performed using two known IE86 binding sequences, CRS and EAIE2 as a competitor. The sequences of the probes were:

```
CRS:        5'-CGTTTAGTGAACCGTCAGAT
            (forward; SEQ ID NO:9)

5'-TCTGACGGTTCACTAAACG
            (reverse; SEQ ID NO:10)

CRSmut:     5'-GCGGCGGTGAACCGTCAGAT
            (forward; SEQ ID NO:11)

5'-TCTGACGGTTCACCGCCGCC
            (reverse; SEQ ID NO:12)

EAIE2:      5'-TAGCGTTGCGATTTGCAGTCCGCTCC
            (forward; SEQ ID NO:13)

5'-GGAGCGGACTGCAAATCGCAACGCT
            (reverse; SEQ ID NO:14)

EAIE2mut:   5'-TAGCGTTGTAACCCATAGTCCGCTCC
            (forward; SEQ ID NO:15)

5'-GGAGCGGACTATGGGTTACAACGCT
            (reverse; SEQ ID NO:16)
```

Figure 9:
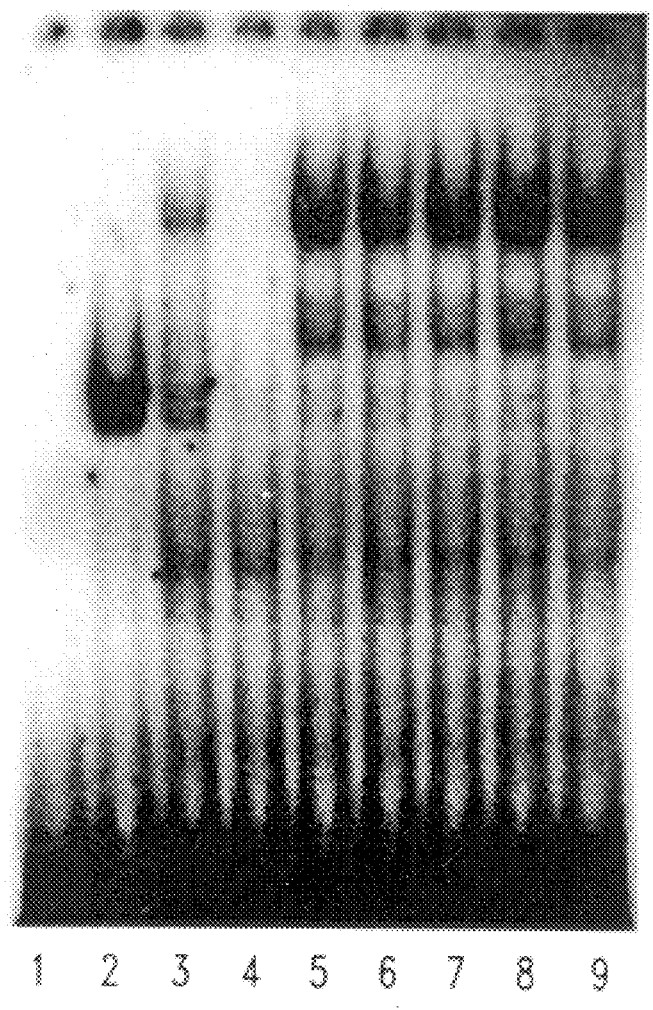
FIG. 9 is an autoradiogram presenting the results of electrophoretic mobility shift assays using the IR1 element and nuclear extracts from IE86-expressing U373MG cells and parental cells. Nuclear extracts were incubated with a radiolabeled IR1 oligonucleotide and 50-fold excess unlabeled competitor as indicated. Arrow indicates specific complex. Lane 1 shows the results in the absence of extract, and lane 2 shows the results in the present of extract from cells that did not express IE86. In lanes 3–9, extracts from IE86-expressing cells were used, in the absence of competitor (lane 3) or in the presence of competitor as indicated (lanes 4–9).

If the IE86 protein binds directly to the IR1 element, one would expect to see competition using excess amounts of the CRS or EAIE2 oligonucleotides. As indicated in FIG. 9, the CRS and EAIE2 wild type as well as mutant oligonucleotides could not compete with IR1 complex (Lanes 6–9). In addition, the IR1 mutant oligonucleotide could not compete. Only the IR1 wild type oligonucleotide was able to efficiently compete with IR1 nucleotide for complex formation. Thus, the data indicate that the IE86 protein does not directly bind to IR1 element.

Example 4

Identification of Sp1 as IR1-bound Protein

This Example illustrates the characterization of a cell-specific IR1-bound protein as cellular transcription factor Sp1 and the effect on pol gene expression of IE86 functional modulation of Sp1.

By computer analysis of the pol promoter sequence subdomain, we found that sequence of the IR1 element is similar to that of cellular transcription factor Sp1 binding site. Therefore, we conducted a competition experiment using Sp1 consensus oligonucleotide and antibody against Sp1 to elucidate whether Sp1 was involved in IE86-mediated IR1 complex formation. The consensus oligonucleotides and antibodies for cellular transcription factors ATF and CREB were used as controls. Sp1 and CREB consensus oligonucleotides were purchased from Promega (Madison, Wis.); polyclonal antibodies against Sp1, ATF and CREB were obtained from Santa Cruz Biotechnology (Santa Cruz, Calif.).

The Sp1 probes were produced as described above by annealing the oligonucleotides, and labeling with [$\gamma$-$^{32}$P] ATP. Reactions were incubated and subjected to PAGE and autoradiography as described above.

As indicated in FIGS. 10A and 10B, the CREB consensus oligonucleotide could not compete with IR1 (FIG. 10A, lane 3). In addition, ATF and CREB antibodies (FIG. 10B, lanes 2 and 3) could supershift the IR1 complex. As expected, we found that both IR1 and Sp1 consensus oligonucleotides (FIG. 10A, lanes 2 and 4) efficiently competed IR1 complex, respectively, and Sp1 antibody supershifted the IR1 complex (FIG. 10B, lane 4). These results clearly indicate that cellular transcription factor Sp1 is in the IE86-mediated IR1 complex, and Sp1 bound to the IR1 element associates with IE86 to form the IR1 complex which mediates pol promoter transactivation.

Example 5

Identification of Repressor Activity in Nonpermissive Cells that Inhibits IE86-Mediated Sp1 Binding Activity This Example illustrates the presence of factor(s) in HeLa cell extracts that inhibit IE86-mediated Sp1 binding to IR1.

As noted above, IE86-mediated transactivation of the pol promoter cannot be detected in HeLa cells. To gain insight into the cell-specific regulation of pol expression, Sp1 DNA binding activity was compared in U373-IE86 and HeLa-IE86 cells using the Sp1 consensus oligonucleotide. The parental U373MG and HeLa cells were used as controls.

Figure 11A:
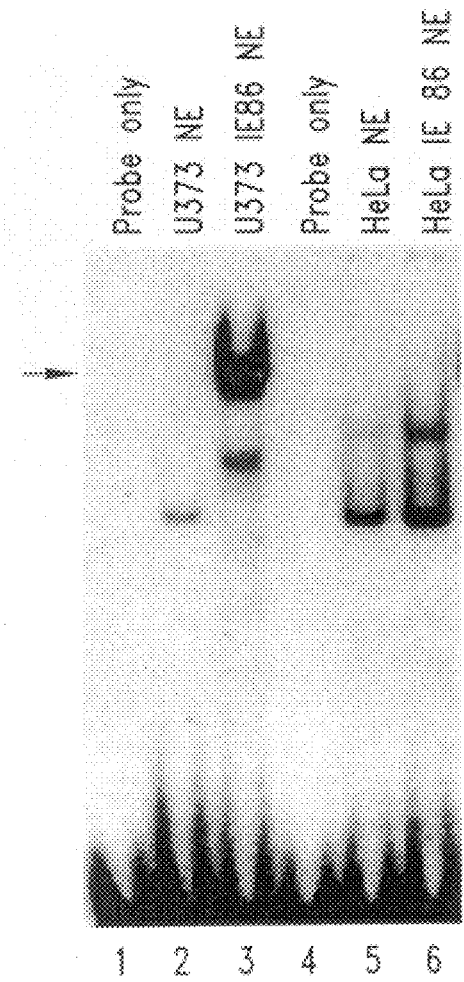
FIGS. 11A and 11B are autoradiograms depicting the results of electrophoretic mobility shift assays performed in the presence and absence of competitor oligonucleotides or specific antibodies.
Figure 11B:
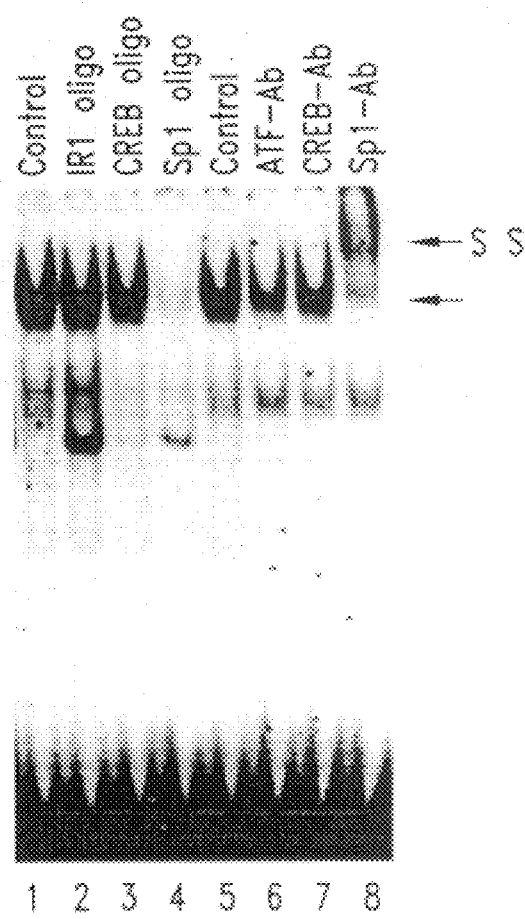

Electrophoretic mobility shift assays were performed as described above. As indicated in FIG. 11A, a dramatic DNA binding activity was detected in U373-IE86 nuclear extracts (lane 3). This activity was specifically competed by Sp1 consensus oligonucleotide (FIG. 11B, lane 4) and supershifted by Sp1 antibody (FIG. 11B, lane 8). However, there was no Sp1 DNA binding activity detected in parental U373MG nuclear extracts (FIG. 11A, lane 2), indicating that the Sp1 DNA binding activity was dramatically increased in the presence of IE86 protein.

To address whether this IE86-modulated Sp1 binding activity resulted from upregulation of Sp1 protein expression or enhancing its binding, Western blot analyses of Sp1 protein levels were performed. These analyses did not detect a significant difference of protein level in U373-IE86 and parental U373MG cells, indicating that IE86 enhanced the Sp1 DNA binding activity in permissive U373MG cells.

Figures 12A, 12B:
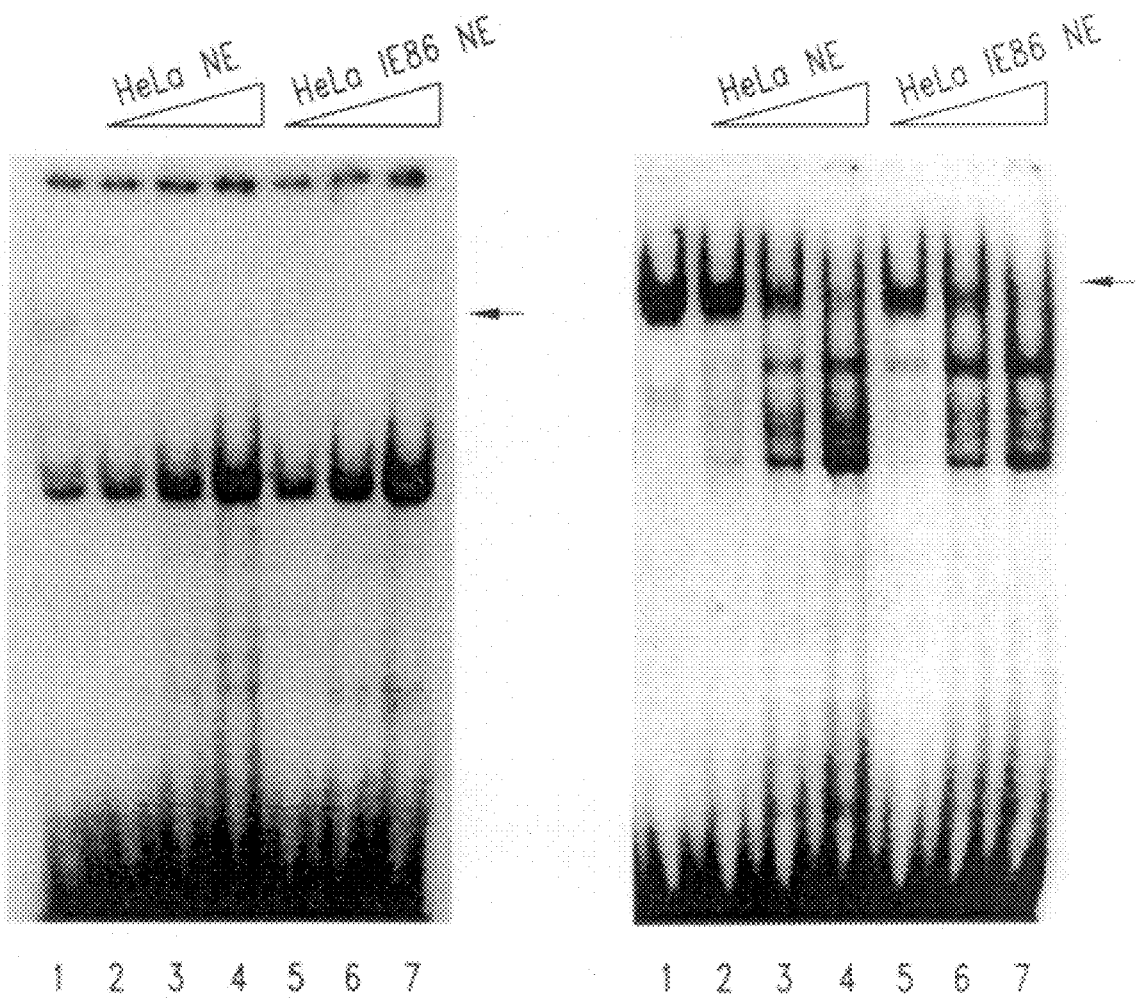
FIGS. 12A and 12B are autoradiograms depicting the results of electrophoretic mobility shift assays performed in the presence of radiolabeled IR1 (FIG. 12A) or Sp1 (FIG. 12B) consensus oligonucleotides, 2.5 μg of U373-IE86 nuclear extract and increasing amounts of HeLa (FIGS. 12A and 12B, lanes 2–4) or HeLa-IE86 (FIGS. 12A and 12B, lanes 5–7) nuclear extracts, up to 5 μg. U373-IE86 nuclear extracts plus probe was used as a control (FIGS. 12A and 12B, lane 1). Arrows indicate IR1 or Sp1 DNA binding.

In HeLa-IE86 or parental HeLa cells, Sp1 binding could not be detected (FIG. 11A, lanes 5-6), suggesting that factor(s) present in HeLa cells inhibit Sp1 DNA binding. Such factor(s) may include a repressor present in HeLa cells, which may inhibit the Sp1 binding activity. To address this possibility, a competition experiment was performed by titration using either HeLa or HeLa-IE86 nuclear extracts. As shown in FIG. 12A, the IE86-mediated Sp1 DNA binding activity was gradually inhibited by increasing amounts of either HeLa (lanes 2-4 compared to lane 1) or HeLa-IE86 (lanes 5-7 compared to lane 1) nuclear extracts. These results indicate that the repressor activity present in HeLa cells is able to inhibit the IE86-mediated Sp1 binding activity, and that IE86 transactivation of the pol promoter is mediated by enhancing DNA binding activity of cellular transcription factor Sp1. The data indicate that both IE86 and cell specific factor(s) may determine promoter-specific transactivation in the cascade of viral gene expression which occurs during the normal life cycle of HCMV.

From the foregoing, it will be appreciated that, although specific embodiments of the invention have been described herein for the purpose of illustration, various modifications may be made without deviating from the spirit and scope of the invention.

We claim:

1. A method for identifying an agent that modulates transcription of HCMV DNA polymerase, comprising:

(a) contacting a nuclear extract prepared from permissive cells expressing IE86 with an oligonucleotide comprising an IR1 element, and with a candidate agent for modulating transcription of HCMA DNA polymerase; and (b) evaluating the effect of said candidate agent on Sp1 binding to said oligonucleotide, and therefrom identifying an agent that modulates transcription of HCMV DNA polymerase.

2. A method for identifying an agent that modulates transcription of HCMV DNA polymerase, comprising:

(a) contacting a nuclear extract prepared from nonpermissive cells expressing IE86 with an oligonucleotide comprising an IR1 element, and with a candidate agent for modulating transcription of HCMV DNA polymerase; and (b) evaluating the effect of said candidate agent on Sp1 binding to said oligonucleotide, and therefrom identifying an agent that modulates transcription of HCMV DNA polymerase.

* * * * *